(12) United States Patent
Clark et al.

(10) Patent No.: US 9,669,231 B1
(45) Date of Patent: Jun. 6, 2017

(54) APPARATUS AND METHOD FOR HYPERTHERMIC TREATMENTS

(71) Applicant: Parmenides, Inc., Franklin, TN (US)

(72) Inventors: George Clark, Indialantic, FL (US); Thomas Otten, Indialantic, FL (US)

(73) Assignee: Parmenides, Inc., Franklin, TN (US)

( * ) Notice: Subject to any disclaimer, the term of this patent is extended or adjusted under 35 U.S.C. 154(b) by 272 days.

(21) Appl. No.: 13/669,094

(22) Filed: Nov. 5, 2012

Related U.S. Application Data

(60) Provisional application No. 61/556,148, filed on Nov. 4, 2011.

(51) Int. Cl.
*A61N 1/00* (2006.01)
*A61B 18/18* (2006.01)
*A61N 2/00* (2006.01)

(52) U.S. Cl.
CPC .................................... *A61N 2/004* (2013.01)

(58) Field of Classification Search
CPC .......... A61N 1/403; A61N 2/002; A61N 2/004
USPC ................. 600/9–10; 607/101–102
See application file for complete search history.

(56) References Cited

U.S. PATENT DOCUMENTS

| 2004/0230263 | A1* | 11/2004 | Samulski ...................... 607/101 |
| 2006/0142748 | A1* | 6/2006 | Foreman et al. ................ 606/27 |
| 2012/0065714 | A1* | 3/2012 | Szasz et al. ................... 607/101 |
| 2013/0237742 | A1* | 9/2013 | Capstick et al. ................ 600/10 |

\* cited by examiner

*Primary Examiner* — Charles A Marmor, II
*Assistant Examiner* — Thaddeus Cox
(74) *Attorney, Agent, or Firm* — Waller Lansden Dortch & Davis, LLP; Mark A. Pitchford

(57) ABSTRACT

A medical apparatus operable to induce localized hyperthermia in a patient via an electromagnetic field emitted by an antenna connected to an output of the medical apparatus includes a signal generator, a bidirectional coupler, and a controller. The signal generator generate radios frequency signal as a function of an operating parameter. The bidirectional coupler provides the radio frequency signal generated by the signal generator to the output and receives a reflected signal from the output. The controller receives the generated radio frequency signal from the signal generator, determines a power of the radiofrequency signal generated by the signal generator, receives the reflected signal from the bidirectional coupler, determines a power of the reflected signal, and determines delivery efficiency of the medical apparatus as a function of the power of the radiofrequency signal generated by the signal generator and the power of the reflected signal received from the bidirectional coupler.

9 Claims, 18 Drawing Sheets

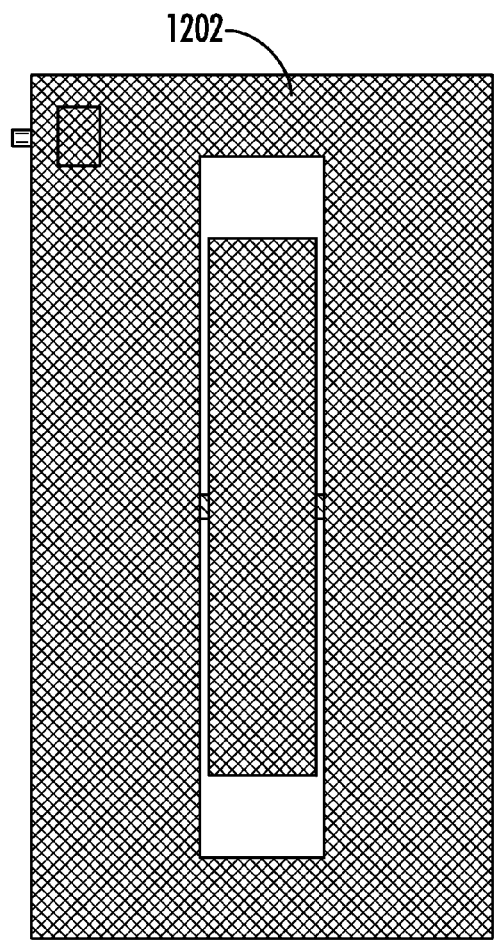
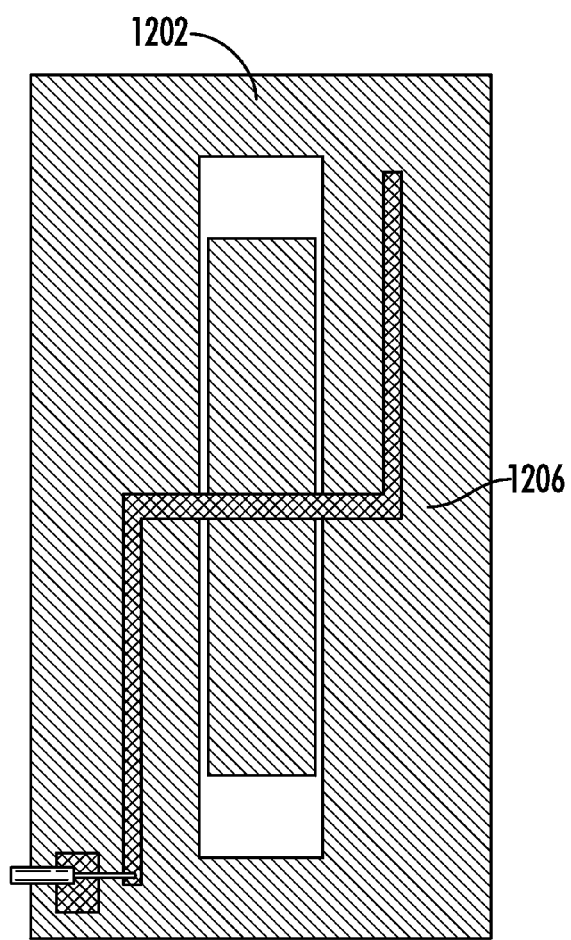
*FIG. 12a*  *FIG. 12b*

APPARATUS AND METHOD FOR HYPERTHERMIC TREATMENTS

CROSS-REFERENCES TO RELATED APPLICATIONS

This application claims benefit of the following patent application which is hereby incorporated by reference: U.S. Provisional Application No. 61/556,148, filed Nov. 4, 2011.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND

The present invention relates generally to apparatuses, systems, and methods for the hyperthermic treatment of patients which can include the co-administration of various pharmaceuticals to the patient. In optional embodiments of the invention, different applicator and antenna designs may be utilized to provide for radiation with different radio frequency signal operating parameters so as to be best applicable to various anatomical sites for various patients. The invention may also include set procedures as well as software for using the applicator to treat a patient.

Hyperthermic therapy is understood to be the exposure of a patient to a higher temperature than their own body temperature. Oftentimes hyperthermia is used as a type of cancer treatment with temperatures of bodily tissue easily exceeding 110° F. or at least 42° C. It is known in the art that higher temperatures can often damage tumor cells including cancer cells while leaving normal tissue cells unharmed. Such application may either shrink or remove tumors from a patient and in some instances may be combined with other treatment options such as chemotherapy and/or radiation to create a synergistic effect in treating the patient. A variety of different cancers may be treated with hyperthermic devices, a sample of which may include brain cancer, lung cancer, melanoma as well as additional other types.

In some hyperthermic treatments, heat may be applied in a localized area which may include the use of microwaves, ultrasound or various types of radiation. Some approaches are external wherein a device is positioned near the desired area for treatment and heating is facilitated. In other styles of treatment, the treatment methods may be described as internal where a probe may be placed within body cavities or alternatively inserted into the tumor directly with heat subsequently applied. In yet further types of hyperthermic treatment, certain treatment styles may include treatment for the entire body which can include placing the patient within a chamber that may raise the body temperature significantly.

A common concern with hyperthermia treatment is the potential discomfort from burns, swelling or other side effects resulting from the heating of an area of a patient's body. A variety of various prior art methods may utilize cooling systems so as to reduce the surface temperature of the skin while still heating the underlying tissue. Unfortunately, such arrangements can be very difficult to coordinate the desired frequency with the desired heating of a tumor and can affect heating depth. While hyperthermia technology has been used for a variety of patients, these previous hyperthermia technologies suffer from limitations including significant side effects to the patient as well as unpredictability of the heating pattern of a patient and limited depth of heating pattern. Additional complications may arise from the possible inadvertent administration of heat and/or electromagnetic radiation to the medical care provider. What is needed, therefore, is an apparatus, method and system of providing hyperthermic treatment to a patient which may be administered for a localized region while being predictable, controllable and easy to monitor so that less energy is used and the chances of side effects are minimized.

SUMMARY OF THE INVENTION

The present invention relates generally to an apparatus, system and method for administering hyperthermia treatment to a patient. In optional embodiments of the apparatus the device may be a medical apparatus operable to determine the delivery efficiency of electromagnetic radiation to a patient.

In one aspect of the invention, a medical apparatus is operable to induce localized hyperthermia in a patient via an electromagnetic field emitted by an antenna connected to an output of the medical apparatus. The medical apparatus includes a signal generator, a bidirectional coupler, and a controller. The signal generator is operable to generate radio frequency signal as a function of an operating parameter. The bidirectional coupler is connected to the signal generator into the output of the medical apparatus. The bidirectional coupler is operable to provide the radio frequency signal generated by the signal generator to the output and to receive a reflected signal from the output. The controller is connected to the bidirectional coupler into the signal generator. The controller is operable to receive the generate radio frequency signal from the generator, determine a power of the radiofrequency signal generated by the signal generator, receive the reflected signal from the bidirectional coupler, determine a power of the reflected signal, and to terminate delivery efficiency of the medical apparatus as a function of the power of the radiofrequency signal generated by the signal generator and the power of the reflected signal received from the bidirectional coupler. Optionally, the medical apparatus may vary the operating parameter, determine the operating parameter variation that provides optimal delivery efficiency, and operate at the determined operating parameter providing optimal delivery efficiency.

In another aspect of the invention, a method of inducing localized hyperthermia in a patient via an electromagnetic field emitted by an antenna connected to an output of a medical apparatus includes generating a radiofrequency signal via a signal generator of the medical apparatus. The radiofrequency signal generated by the signal generator is provided to the output of the medical apparatus via a bidirectional coupler of the medical apparatus. A reflected signal is received from the output at the bidirectional coupler. The generated radiofrequency signal from the signal generator is received at a controller of the medical apparatus. The controller determines the power of the radiofrequency signal generated by the signal generator. The reflected signal is received at the controller from the bidirectional coupler.

The controller determines a power of the reflected signal. The controller then determines a delivery efficiency of the medical apparatus as a function of the power of the radiofrequency signal generated by the signal generator and the power of the reflected signal received at the processor from the bidirectional coupler.

In additional optional embodiments of the invention, the applicator may be designed for a specific frequency so that the applicator can be tailored to provide heat at a specified depth within a patient. More particularly, the applicator optionally may be anatomically designed to fit a specific size and location of a patient so that optimal contact of the applicator to the individual's skin is achieved. More particularly, optional embodiments of the applicator may include an applicator that operates at 434 MHz or alternatively an applicator that operates at 915 MHz as both frequencies have proven to be useful in administering electromagnetic radiation to individuals for the purpose of hyperthermia treatment.

Additional optional embodiments may include the use of software to control a pulsing or constant application of electromagnetic radiation to an individual for the purpose of hyperthermic treatment. Therefore, there is software designed to allow one to make the necessary choices in administering the treatment as desired by the health care provider to the individual needing hyperthermic treatment.

An optional aspect of the present invention is to provide an applicator for hyperthermia treatment that may be used in direct contact with the patient's skin for providing heat.

Another optional aspect of the invention is an applicator that provides a specific frequency so that penetration to a specific depth within the patient is known.

Yet another optional aspect of the invention is an applicator for administering electromagnetic radiation that is sized for use at specific anatomical locations on a patient.

Yet a further optional aspect of the invention is a method of treating various ailments ranging from muscular issues to cancer.

Still a further optional aspect of the invention is a system including the use of electromagnetic radiation to raise the temperature of a localized region of a patient while administering a drug to the patient so that a synergistic effect is achieved at the site of the electromagnetic radiation.

In accordance with the purpose of the invention, as embodied and described herein, the invention in optional embodiments may include an applicator for administering electromagnetic radiation at a desired frequency to a patient having an ailment which may be treated through hyperthermia. The invention may be utilized with patients ranging from various types of animals including horses, cats and dogs to humans as well.

The applicator of further optional embodiments may incorporate a variety of different designs so as to be used for various locations on or in the patient's body. As used herein the term "patient" means any animal as well as human that may benefit from a hyperthermia treatment. While some patients may have physical ailments such as cancer, it is conceivable that other patients may only have simple aches and pains which may also benefit from the administration of hyperthermic treatment through the use of the invention as described herein.

The accompanying drawings are incorporated in and constitute part of the specification. The drawings illustrate optional embodiments of the invention and together with the description serve to explain some principles of the invention.

BRIEF DESCRIPTION OF THE SEVERAL VIEWS OF THE DRAWINGS

FIG. 12A is a top perspective view of a bottom laminate of an antenna without a slot.
FIG. 12 B is a top perspective view of a top laminate and a bottom laminate of the antenna of FIG. 12A.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of the embodiments described herein, a number of terms are defined below. The terms defined herein have meanings as commonly understood by a person of ordinary skill in the areas relevant to the present invention. Terms such as "a," "an," and "the" are not intended to refer to only a singular entity, but rather include the general class of which a specific example may be used for illustration. The terminology herein is used to describe specific embodiments of the invention, but their usage does not delimit the invention, except as set forth in the claims.

Terms such as "providing," "processing," "supplying," "determining," "titrating," or the like may refer to an action of a computer system, computer program, processor, logic or alternative analog or digital electronic device that may be transformative of signals represented as physical quantities, whether automatically or manually initiated. As used herein, a "bidirectional coupler" may refer to a duplexer, a circulator, or any other component enabling duplex communication or signal transmission in a single medium.

Figure 1:
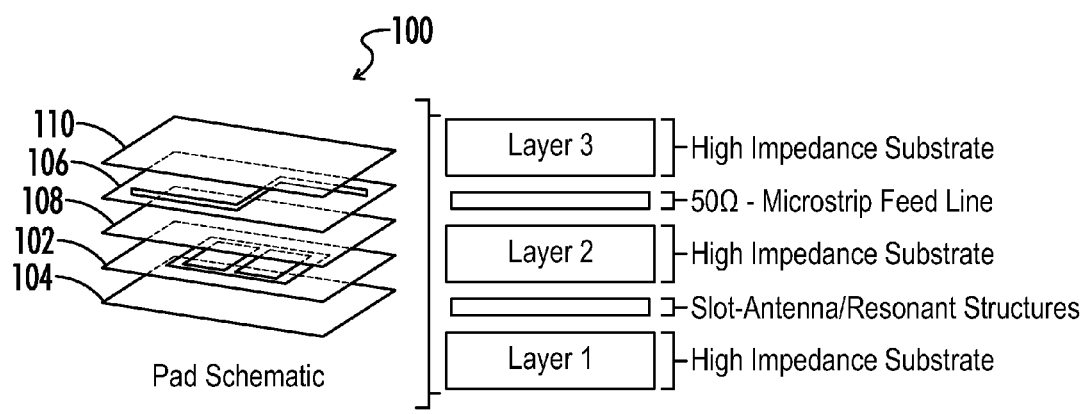
FIG. 1 is an exploded diagram of an applicator.

Referring now to the figures, FIG. 1 is a schematic illustration of an applicator of the present invention. As is illustrated, there may be a variety of different layers in forming the applicator 100 for administering electromagnetic radiation to a patient. Generally, the antenna 102 comprises the major portion of the applicator 100 and is the portion responsible for creating the electromagnetic field for inducing localized hyperthermia in the patient. In optional embodiments of the antenna 102, the antenna 102 may have dimensions of about 11 cm×15 cm×1.5 cm as such size may work with a variety of different anatomical locations on a patient's body. The layer in contact with the skin, the lowest layer 104 of the design, is generally understood to be a high impedance substrate. Generally the high impedance substrate can be understood as being an insulating layer and can be formed from a piece of flexible silicone. While other materials may be used as a high impedance substrate, the use of flexible silicone can possibly be advantageous as it allows a flex of the antenna so that the antenna 102 may be in greater physical contact with the surface of the patient then if the high impedance substrate was rigid and would not allow for flex of the antenna 102.

The next layer can be understood to be the slot antenna 102. Generally, the layer that forms a slot antenna 102 may be understood to be formed of a metallic material which may optionally be copper on top of a printed circuit board (PCB). In optional embodiments, the PCB is also flexible so as to allow for conformal application to a variety of anatomical sites. As used herein, the term "slot antenna" generally describes the use of a metal material, usually in a flat arrangement, with either a whole slot or opening cut away. Slot antennas function similarly to dipole antennas in that when driven by a specific frequency the slot radiates electromagnetic waves based on the configuration of the slot as well as the frequency, both determining the distribution pattern of the radiation. Additionally, the length and width of the slot within the antenna can determine the impedance of the slot antenna 102. In optional embodiments of the invention, the aperture in the slot antenna 102 may measure approximately 35 cm² to about 45 cm² and in further optional embodiments may measure about 35.9 cm². In forming the applicator 100, an additional layer of a high impedance substrate 108 may be placed above the slot antenna 102 with a feed line 106 being there on top. In optional embodiments, the microstrip feed line 106 is also fabricated using a PCB and can be used to help convey radiofrequency and/or microwave frequency signals. In additional optional embodiments, the microstrip feed line 106 may be a 50 ohm microstrip feed line. An additional high impedance substrate layer 110 may be positioned on top of the feed line 106 layer with all layers combined together to provide for a flexible applicator 100. An additional shielding layer (see FIG. 2 at 202) may be on top of the top layer 110 of the high impedance substrate which may provide shielding qualities so that electromagnetic radiation is directed toward the patient and blocks from a mission toward a caregiver (e.g., veterinarian, doctor, or nurse) or user of the medical apparatus and applicator 100.

In further optional embodiments the applicator may additionally include a thermosensor (i.e., temperature sensor, see FIG. 3 at 302) incorporated into the applicator 100 to allow for treatment, monitoring and control while administering heat to a patient. Through use of the thermosensor which may be integrated into the device, a provider can understand and realize the surface temperature of the patient's skin adjacent the applicator 100 and thus adjust the medical apparatus accordingly if discomfort or other issues are noted.

Figure 2:
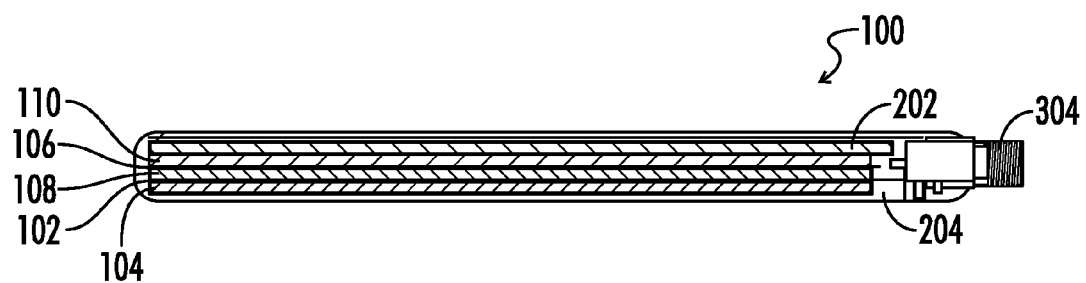
FIG. 2 is a side cross-section view of an applicator.

In additional optional embodiments of the applicator 100, the applicator 100 may include a stiffener within the applicator so that the applicator maintains a rigid formation. Optional embodiments of this design may include a polyimide stiffener as the middle layer 108 or in the middle layer so as to provide stiffness to the applicator 100. In one embodiment, the stiffener is a small structure in the vicinity of the cable connector 304 and the temperature sensor 302 which provides structural strength in the region of these connectors. As illustrated in FIG. 2 there is the thickness of the applicator design showing the layers in contact with one another as how the device would be used when applied to patients in certain optional embodiments. The applicator 100 thus may have a thickness somewhere between about 0.3 inches to about 0.4 inches and in other optional embodiments may include a thickness of about 0.32 to about 0.37 inches. This applicator in optional embodiments may also include a cover coating 204 to combine all the layers and hold the layers together while protecting aspects of the applicator 100. The cover coating 204 may range from about 0.02 to about 0.08 inches thick and in further optional embodiments may comprise a covering 204 of about 0.04 inches thick.

Figure 3:
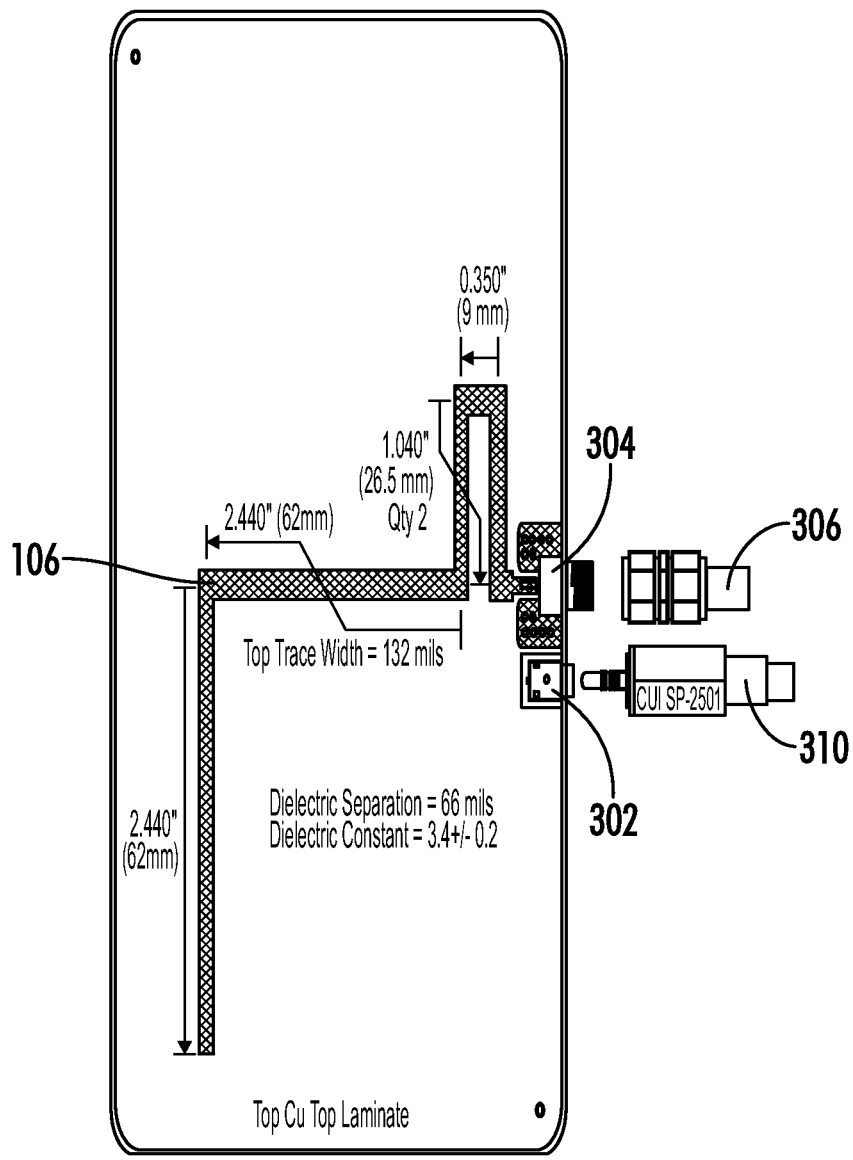
FIG. 3 is a top perspective view of a top laminate of an applicator.

Referring now to FIG. 3, there is an illustration of the top laminate 106 including the microstrip having inputs for various devices. As is illustrated, optional embodiments may include a radio frequency (RF) connector 304 with the connector being connected to the top side of the laminate so as to provide the necessary connection for the connector cable 306 to the output of the medical apparatus. The second connector 302 is in optional embodiments attached to the bottom laminate with the antenna and can provide a connection to the temperature sensor 302. Generally, access may be provided through the top laminate via a cut out which may allow the top laminate unrestricted motion at this point and help avoid situations where the laminate may buckle. In yet further optional embodiments, the second connector 302 may be a quick disconnect miniature stereo jack which may prevent interconnect failure due to solder fraction if the cable is yanked.

Figure 4:
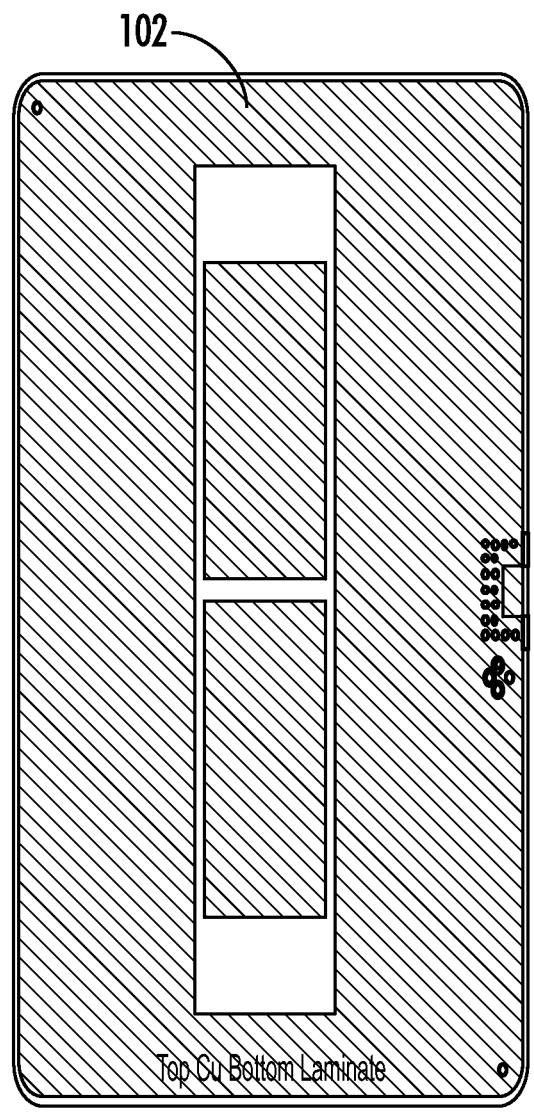
FIG. 4 is a top perspective view of a bottom laminate of an applicator.

FIG. 4 is a top view of the bottom laminate having the antenna 102 and further provides optional arrangements for the gap width. As is illustrated in this optional embodiment of the antenna there is a 0.565 gap width for this configuration. Generally, this slot antenna 102 is separated from the microstrip feed line 106 by a silicone pad 108 which is generally of from about 0.04 inches thick to about 0.08 inches thick and in optional embodiments may be about 0.062 inches thick. As previously discussed, both the top and bottom silicone pad 110, 104 may be the same thickness. They can serve to cushion the top and bottom laminates 106, 102 from outside impact as well as to cover protrusions from the connectors at the top and also cover the protrusion resulting from the temperature sensor 302 that in optional embodiments is attached to the bottom of the bottom laminate 102.

Generally the laminates are described as flexible and the laminates may be understood to have various thicknesses though in optional embodiments may be about 0.004 inches thick. Various connector cables 306 and temperature sensor cables 310 will often have to be used with the invention with cable lengths running anywhere from a couple feet to multiple feet in length to allow applicator 100 operation and evaluation at greater distances so as to be convenient for the health care provider and the patient.

Figure 5A:
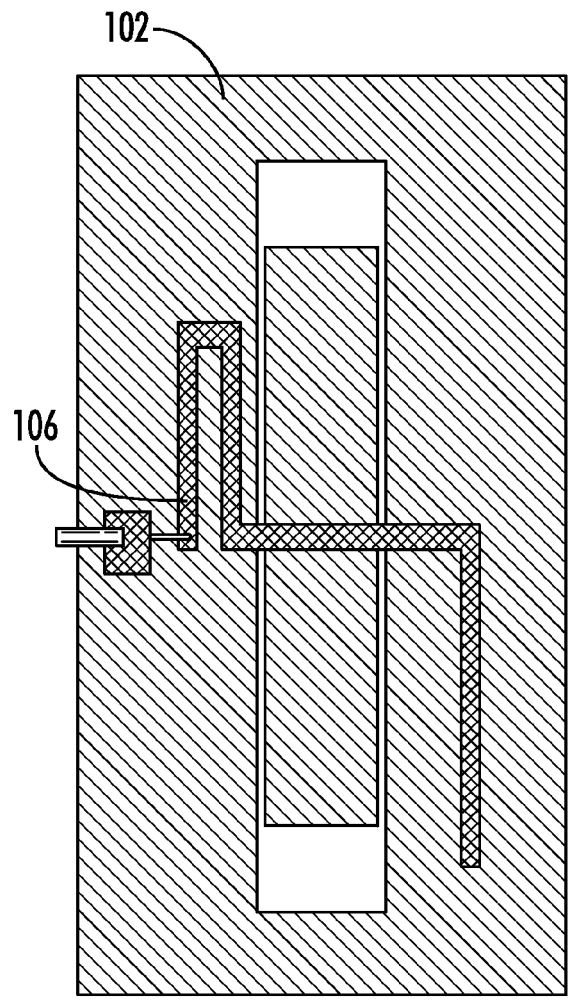
FIG. 5A is a top perspective view of a top and bottom laminate of an applicator.
Figure 5B:
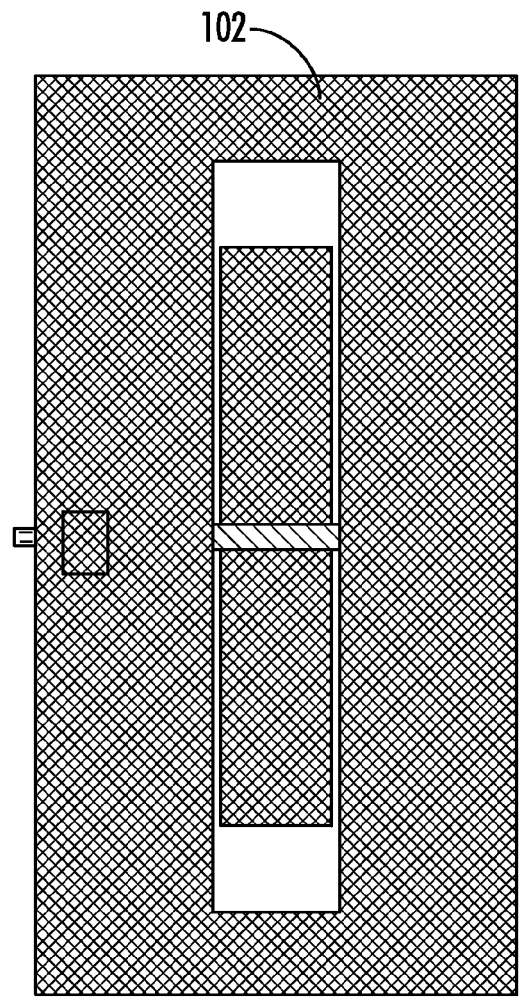
FIG. 5B is a top perspective view of the bottom laminate of the applicator of FIG. 5A.

In further optional embodiments the antenna 102 of the applicator may take on various configurations especially when situated with the feed line 106. FIGS. 5A and 5B illustrate a partial schematic view of an applicator 100 for both the feed line as well as the antenna 102 which is used typically at about 434 MHz (e.g., 400 to 460 MHz). Generally dimensions for this type of antenna 102 have been found to be useful at about 150 mm by about 110 mm though in further optional embodiments this may be larger or smaller. As seen in these illustrations there is a view of a feed line 106 in FIG. 5A and a view of the antenna with gap that reveals the feed line 106 crossing the antenna 102 in FIG. 5B. Generally this antenna is utilized with a radio frequency transceiver operating at about 434 MHz (e.g., 400 to 460 MHz) which optionally may have a variable power output. The power for such systems of this invention may vary anywhere from about 5 watts to about 40 watts though in other optional embodiments may vary from about 5 watts to about 20 watts depending upon the application intended patient type. In tailoring the invention for treatment of patients and the necessary interaction of electromagnetic fields with tissue, variables should be defined to determine delivery effectiveness of the device. One such parameter includes a specific absorption rate which generally provides estimates of the total real power that is transmitted into the tissue. Additionally return loss is generally understood to reflect the measurement of reflected energy as a result of the mismatch between the applicator and the tissue impedance. Through the use of these variables, one is able to determine the efficiency (i.e., delivery efficiency) of energy transferred for different applicator 100 locations, antenna configurations (i.e., feed strip line 106 and slot antenna 102 sizes, shapes, and spatial relationships), and operating parameters of a radio frequency signal driving the applicator 100 in dealing with patients.

Figure 6:
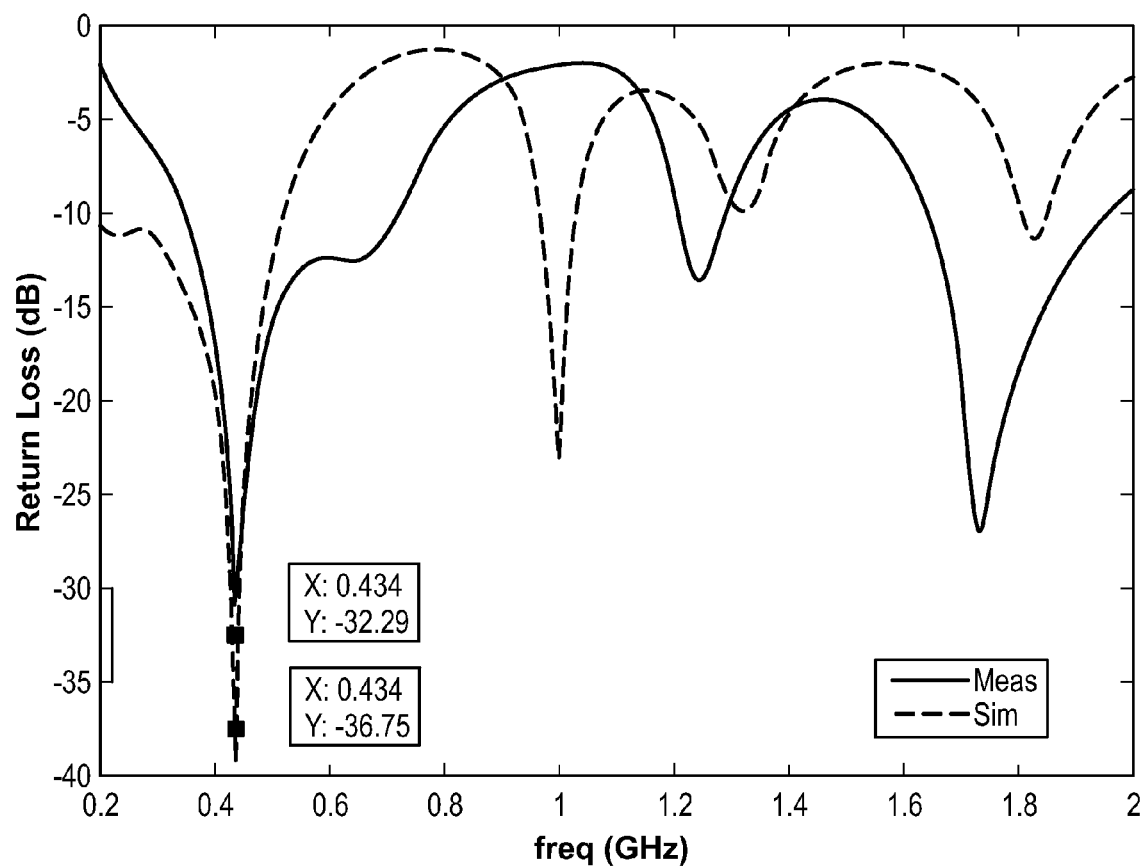
FIG. 6 is a graph of actual and simulated measurements of reflected power (i.e., return loss) for the applicator of FIGS. 5A and 5B.

FIG. 6 is an illustration of actual and simulated measurements for an applicator 100 as configured in FIGS. 5A and 5B which shows return loss (i.e., reflected power) for various frequencies of a radio frequency signal driving the applicator 100. As is illustrated, the simulations match the measured values best at about 434 MHz (i.e., 400 to 460 MHz) with acceptable tissue matching between tissue and the applicator 100 being defined as return loss of less than about 10 decibels. In examining and testing the applicator 100 having the configuration as described in FIGS. 5A and 5B, measurements can be made in connection with various anatomical locations for a variety of patient species to determine optimal applicator designs (i.e., size, shape, and spatial relation of the feed line 106 and slot antenna 102) and the frequency, duty cycle, pulses per second, and power level of the radiofrequency signal driving the applicator 100.

Figure 7:
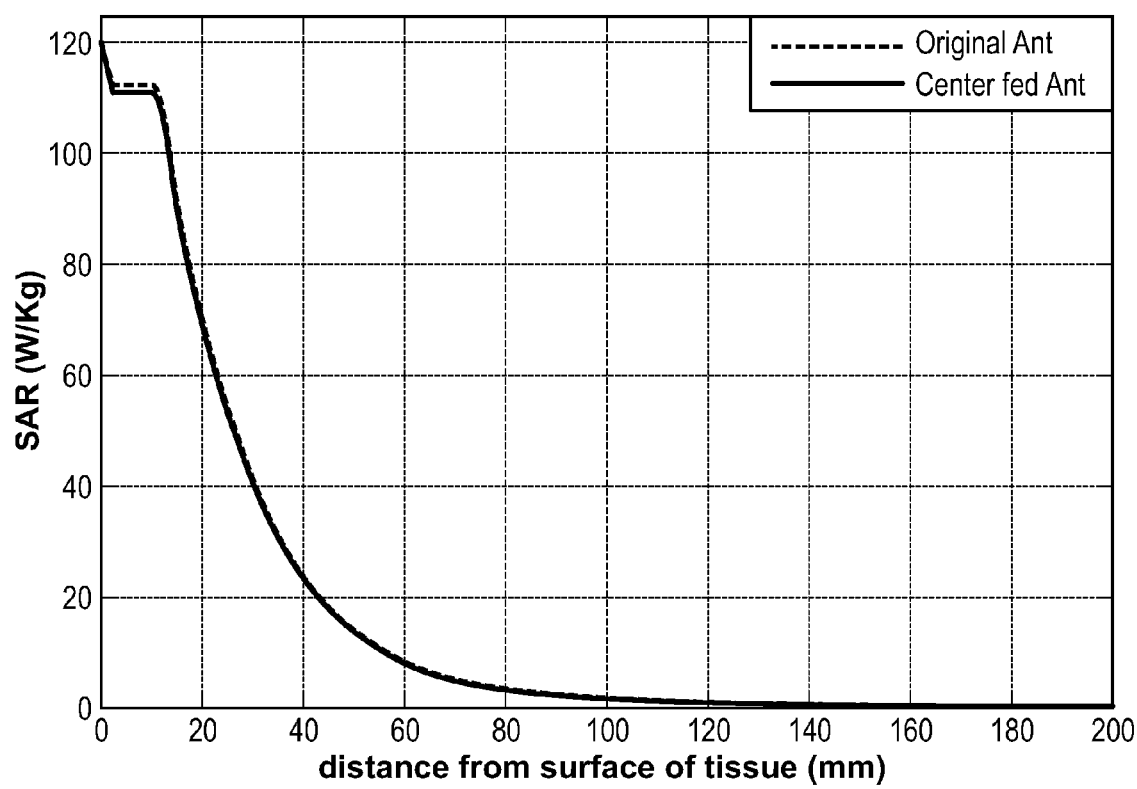
FIG. 7 is a graph of absorption rate versus distance from the surface of the tissue for the applicator of FIGS. 5A and 5B at a frequency of 434 MHz.

FIG. 7 illustrates the specific absorption rate versus distance from the surface of the tissue for the applicator 100 as illustrated in the schematically in FIG. 5A and FIG. 5B driven by a radiofrequency signal at 434 MHz. As is illustrated, the further the antenna 102 is from the tissue, the lesser absorption of electromagnetic field there is by the patient with there being a significant drop once the distance is greater than about 10 mm from the surface of the tissue.

Figure 8:
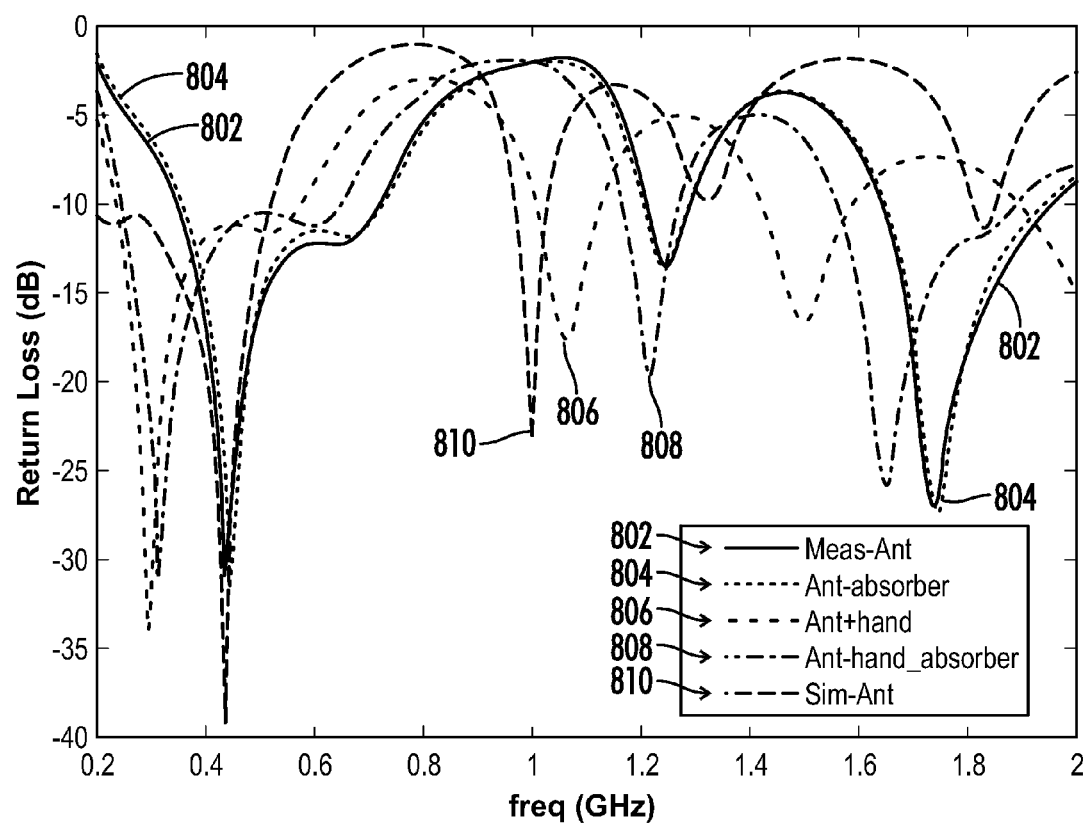
FIG. 8 is a near field representation of the electromagnetic field for the applicator of FIGS. 5A and 5B when used with a backing plate or shield layer.

FIG. 8 illustrates the effect of various backing plates (i.e., shield layer 202) or other items put on the back side of the antenna (i.e., slot antenna 102 and feed line 106) for directing the field toward the patient. As is illustrated, the measurements 804 of the antenna illustrating the lowest return loss at 434 MHz using an absorber, the same effectiveness was found with the general shape very closely nearing that of the antenna alone 802. Alternatively, the positioning of a user's hand, generally the health care practitioner, significantly shifted the frequency as is illustrated by both the antenna and hand line 806 and the antenna, hand, and absorber line 808. Thus, as demonstrated, physical arrangement of patient and caregiver a relatively insignificant effect on the absorption by the patient, and as discussed below, a control unit of the medical apparatus including the applicator 100 may automatically compensate for such shifts by optimizing the frequency a radiofrequency signal driving the applicator 100, optimizing the duty cycle of the radiofrequency signal driving the applicator 100, optimizing the pulses per second of the radiofrequency signal driving the applicator 100, and/or optimizing the power level of the radiofrequency signal driving the applicator 100. The antennae simulation 810 generally tracks the frequency response of the measured antenna 802 and the antenna with the absorber 804. As such, a simple absorber may not be a significantly useful material because a hand on the back side of the applicator 100 significantly altered the electromagnetic field as intended to flow within the localized area of the patient.

Figure 9A:
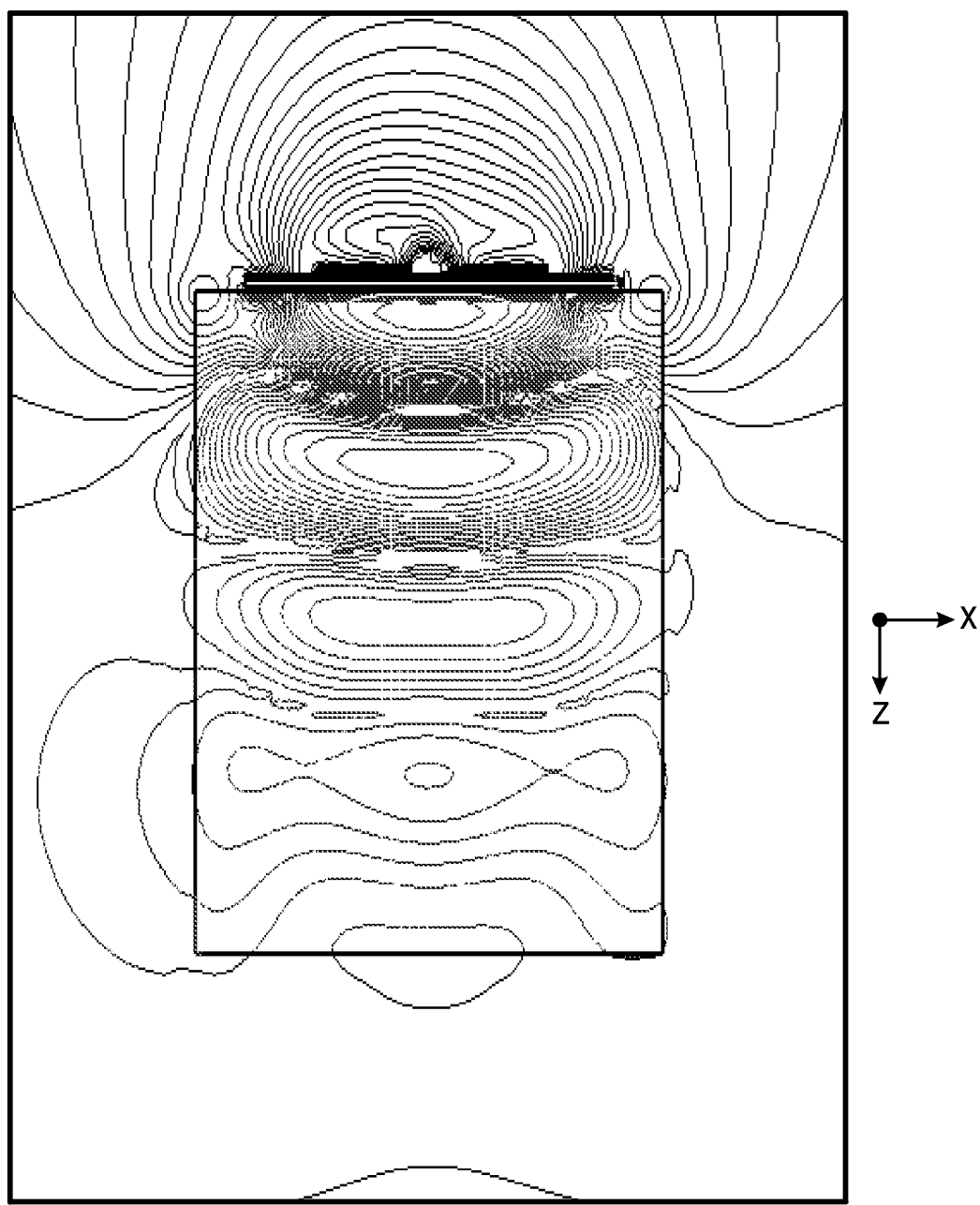
FIG. 9A is a near field representation in the X-Z plane for the applicator of FIGS. 5A and 5B driven at 434 MHz.
Figure 9B:
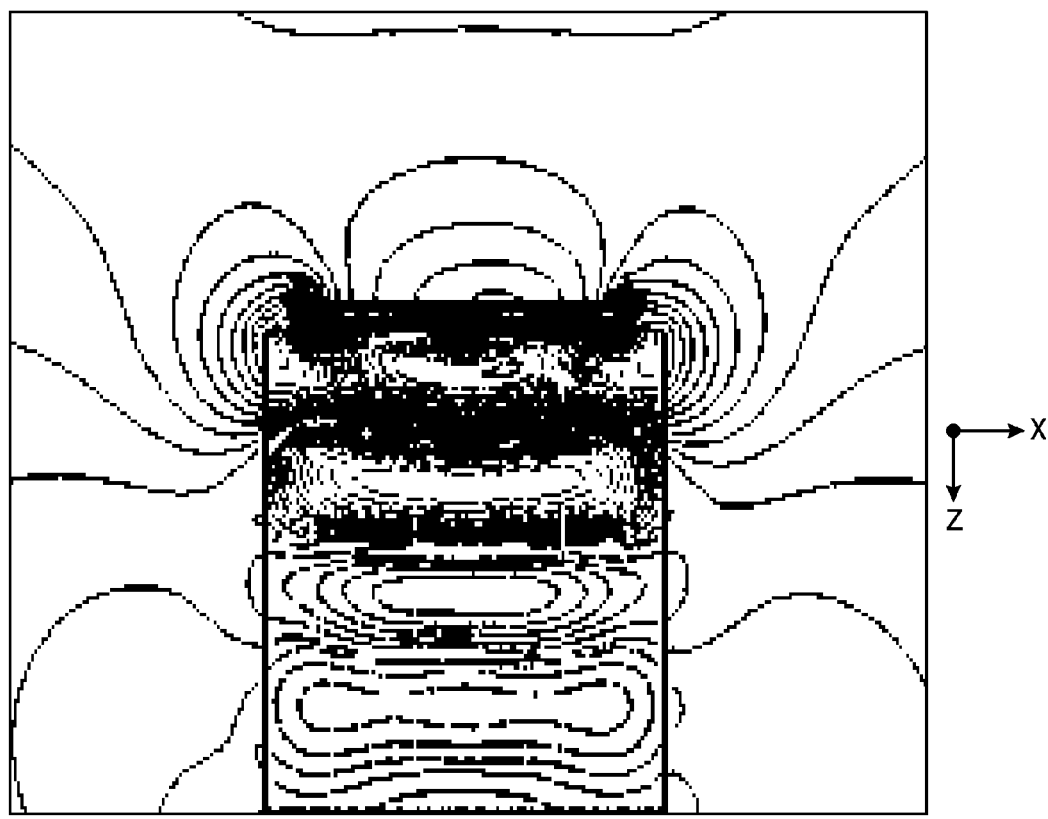
FIG. 9B is a near field representation in the X-Z plane for the applicator of FIGS. 5A and 5B driven at 434 MHz and including a backing plate or shield.

FIG. 9A provides a near field representation for the antenna of the present invention in the x-z plane when the applicator 100 is above tissue and energized at approximately 434 MHz. As is illustrated from this representation this optional embodiment of the antenna configuration provides a relatively uniform electromagnetic field across the length of the antenna and penetrates fairly deep within the soft tissue boundary while exhibiting a lesser effect on the skin's surface. FIG. 9B is a similar near field representation for the antenna as described previously though includes a shield which improves the directivity and substantially reduces back field radiation that is illustrated in FIG. 9B. Otherwise stated, the addition of a floating shield plate above the antenna (i.e., slot antenna 102 and feed line 106) eliminates to a significant degree the back field irradiation.

Figure 10:
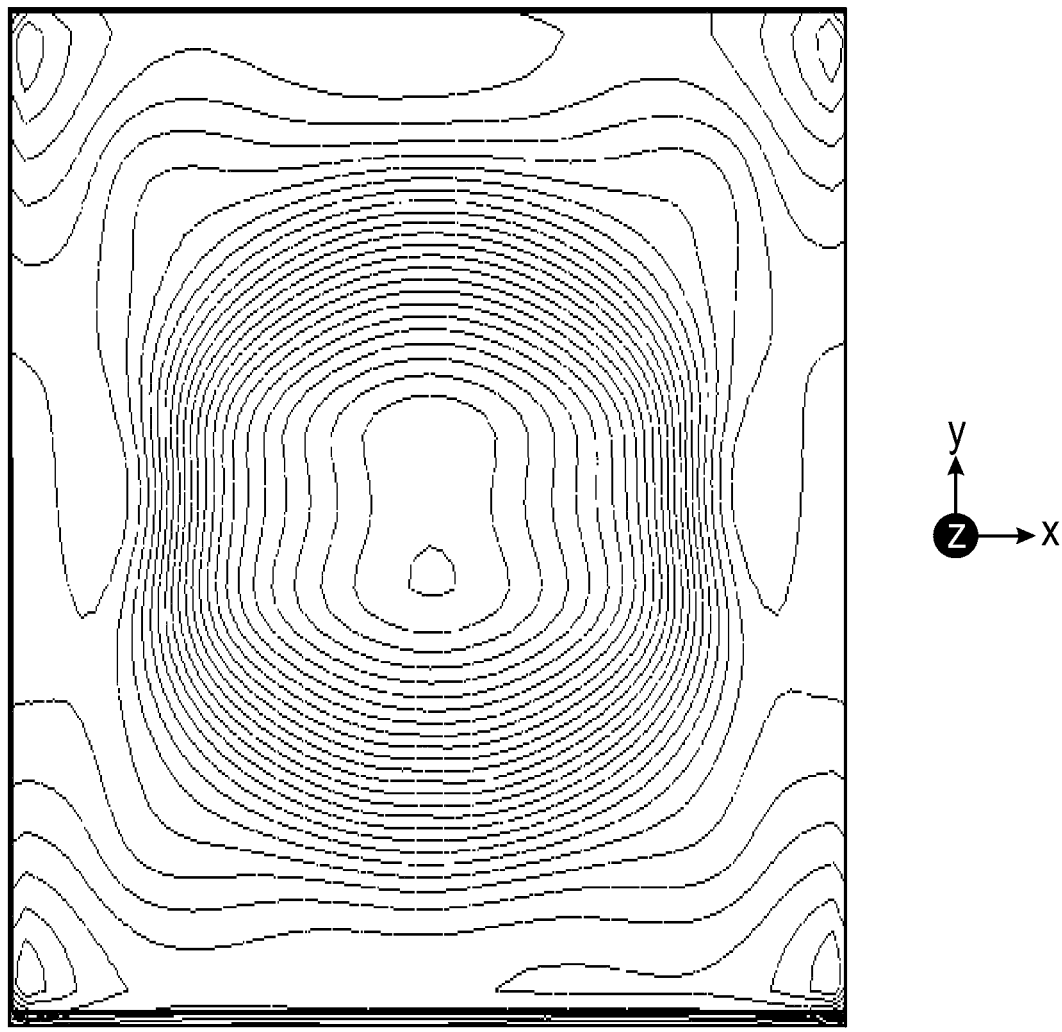
FIG. 10 is a near field representation at about 1 cm depth in the local area of the patient adjacent the applicator of the medical apparatus.

In illustrating the general size or area of the electromagnetic field in the x-y axis, FIG. 10 shows a representation of the electromagnetic field at about a 1 cm depth in the local area of the patient. Additionally, simulations for calculating a specific absorption rate show that the antenna design of this embodiment as previously illustrated in FIGS. 5A and 5B has a tissue penetration depth of over 4 cm and generally may be about 4.59 cm though in other optional embodiments, the tissue penetration depth may differ.

Figure 11A:
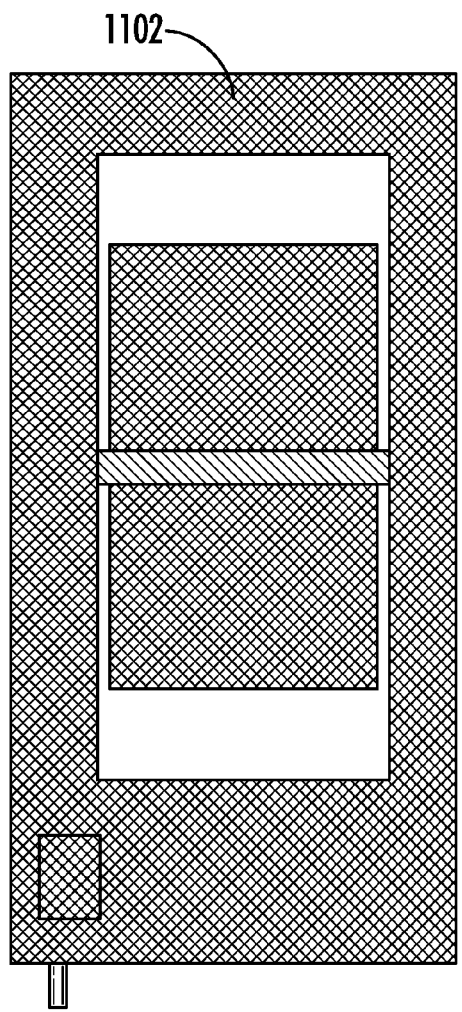
FIG. 11A is a top perspective view of a top and bottom laminate of a half-size applicator.
Figure 11B:
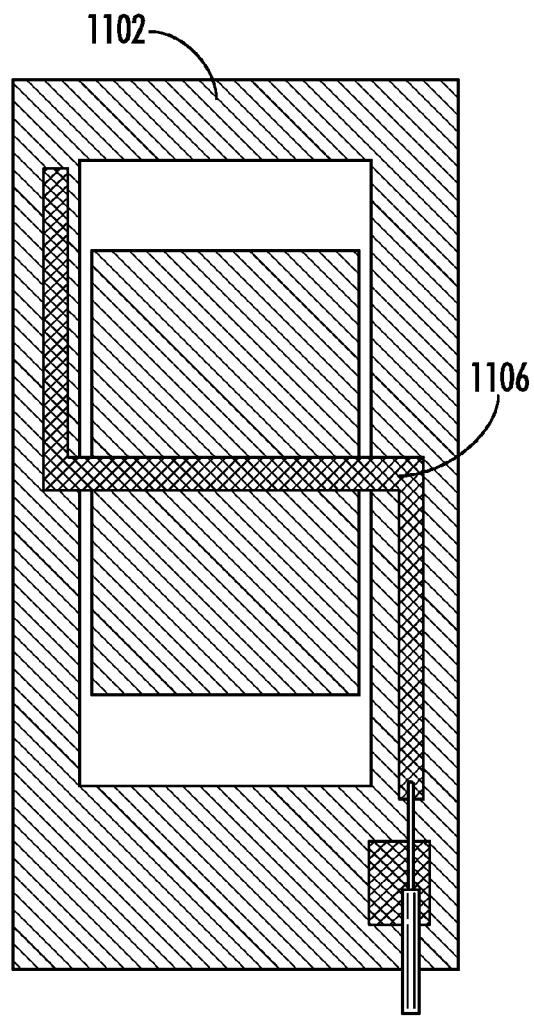
FIG. 11B is a top perspective view of a bottom laminate of the half-size applicator of FIG. 11A.
Figure 13:
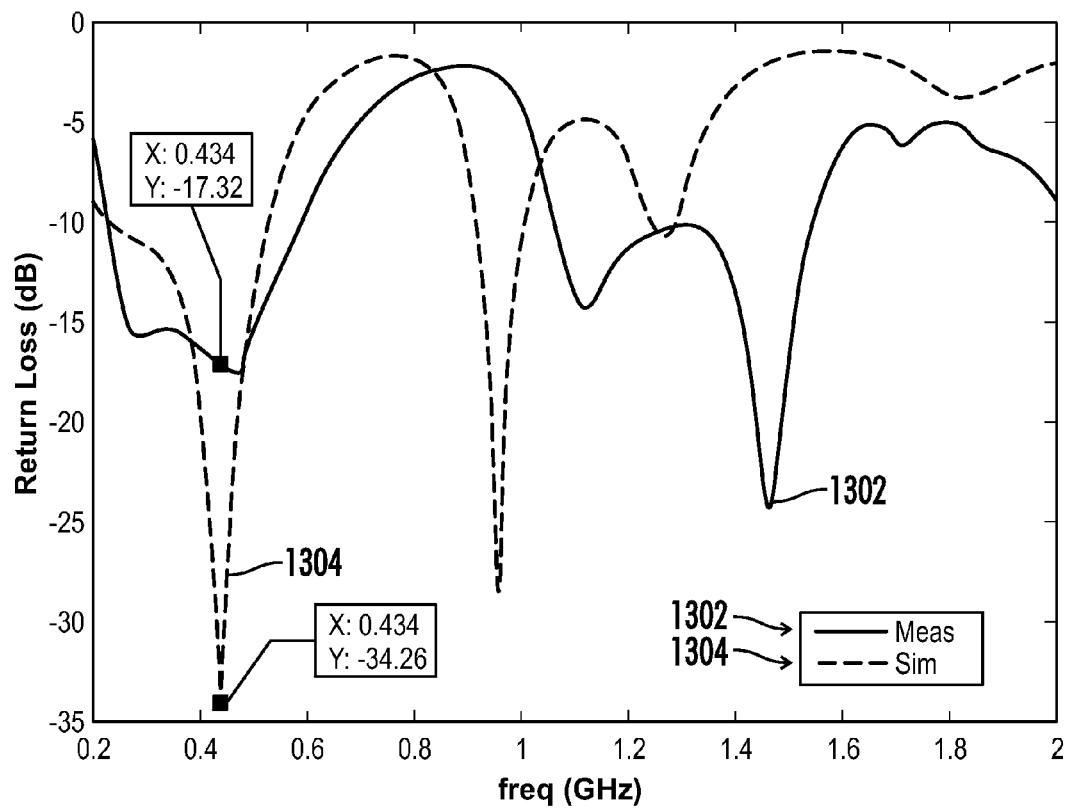
FIG. 13 is a graph of the return loss versus frequency for the antenna of FIGS. 12A and 12B.

FIGS. 11A and 11B provide further optional embodiments of portions of the applicator 100 that may be used for the present invention with the antenna (i.e., slot antenna 1102 and feed strip 1106) having a half size of the antenna (i.e., slot antenna 102 and feed strip 106) as previously illustrated in FIGS. 5A and 5B. In optional embodiments, this antenna (i.e., slot antenna 1102 and feed strip 1106) may have dimensions of approximately 75 mm by 110 mm. Advantages that may be present from the half size designs may be the ability to place the half size applicators at anatomical locations where the larger size applicators and antennas would not fit. As previously described, the applicator performs best when in contact with the skin. With the half size configuration, certain locations can be better managed and thus better treatment can occur. Other optional embodiments for the applicator design may include designs such as in FIGS. 12a and 12b which illustrate different configurations of the antenna (i.e., slot antenna 1202 and feet strip 1206) as the gap between the two small patches is removed. This is best illustrated in FIG. 12A. FIG. 13 is a graph of the return loss (simulated 1304 and actually measured 1302) versus frequency for the antenna design illustrated in FIGS. 12A and 12B and as is readily apparent this antenna design has different characteristics regarding the return loss as the measured value only has a return loss of about −17 dB at 434 MHz compared to about −32.29 dB as measured for the antenna designs illustrated in FIGS. 5A and 5B.

There are additionally other types of antennas that may be utilized and applicant is not limited through his disclosure to any of the designs but rather intends to provide these examples to show how various antennas can be used with applicant's invention. For example, there may be different antenna designs which generally can include dimensions of about 98 mm to about 110 mm.

Optional embodiments of the invention may include other frequencies and may be used to generally include the same component parts that may be used with or without a shield on the top surface. Two wavelengths that have been used in various optional embodiments of the present invention include 434 MHz and 915 MHz though other frequencies may be selected and utilized. Generally these frequencies pair best with the animal tissue (i.e., the local area of the patient adjacent the applicator or antenna) with the specific antenna design as described here within the application.

For various applications where the applicator 100 may not be in direct contact with the patient's body, the frequency of the radiofrequency signal driving the applicator 100 may have to be adjusted so that proper penetration with the tissue is achieved. In various optional embodiments of the invention, the high impedance substrates are interspaced between the microstrip feed line and the antenna with a shield typically on the outermost high impedance substrate. The invention may include a coupler for connection to provide for connection with a radiofrequency transceiver. Other connections of the applicator 100 may be for a temperature sensor or probe which can measure the surface temperature of the user's skin.

The applicator 100 of the present invention includes a variety of traits, one of which may optionally be having a flexible construction. As the surfaces of patients are rarely completely flat, the flexible construction allows for the applicator 100 to be in direct contact with the patient and thus provide for the effective transfer of electromagnetic energy to the patient. Advantageously, the invention may include optional embodiments with the feed line in a central position and fixed relative to the slot antenna to maintain a location with respect to the other layers of the antenna to provide for field consistency.

In one embodiment, the high impedance substrate layers 104, 108, and 110 and optional embodiments have a dielectric constant between about 2.5 and 3.5 which may be selected based upon the specific tissue composition for which treatment is sought. Most often the substrate is a silicone polymer which can be varied based upon a species and the anatomical site to be treated.

The invention of this application allows a user to test the permittivities for different species and locations on different species and thus optimize construction of the antenna with the specifically desired dielectric constant of the substrate material that provides for the best performance. In further optional embodiments, the system as a whole can detect reflected power while in use so a user can reposition the antenna and optimize a radio frequency signal driving the antenna to maximize energy delivery to the patient. Various options exist for controls for the invention with systems ranging from a simple on or off of the radiofrequency signal driving the antenna operating at a set frequency and power level to a series of pulses (i.e., pulse width modulated) or otherwise pre-specified arrangements. In optional embodiments, radiofrequency pulses may be about one millisecond in length at a desired frequency with a user able to vary parameters to achieve an in vivo electroporation effect within the electromagnetic field generated by the applicator 100. Electroporation may advantageously lead to increased cellular uptake of macromolecules within the electromagnetic field and thus may be of use when administering a pharmaceutical agent (i.e., chemotherapy). For a variety of the various optional embodiments as have been discussed, the frequency of the radiofrequency signal driving the antenna is generally determined to be from about 434 megahertz to about 915 megahertz with the antennas and applicators designed to focus an electromagnetic field at a desired point underneath the skin of the patient.

This may be optionally based upon the frequency transmitted from the signal generator, the power of the signal generator, the dielectric constant of the substrate used in the antenna, the configuration of the antenna, and additionally the material used to make the antenna. Optionally, the user also has the capacity to consider the various properties of the tissue to be treated in the patient so that the energy transferred to the patient is optimally used.

Furthermore, as previously discussed, a shield may be placed in the back layer to block radiation being reflected away from the tissue and thus both shield the healthcare provider while simultaneously providing more energy to the patient who is the intended recipient.

Further features of optional embodiments of the present invention may include a temperature control and sensor that may maintain the substrate (and therefore the skin adjacent the applicator) at or below a predetermined threshold temperature. In these optional embodiments, the temperature sensor may be placed centrally in the antenna although in other optional embodiments, the temperature sensor may be located at various locations upon the antenna which may in part be based upon the size of the applicator as well as the specific anatomical location for which the applicator will be used.

Optional aspects of the present invention may include a 50 ohm transmission line (i.e., connector cable 306) used with the medical apparatus and antenna though different transmission lines may be used depending upon the application, the desired applicator as well as what is needed for the patient. In one embodiment, the connector cable 306 is 4 feet long and has a cable loss of 0.129.

The antenna as used in optional embodiments of the present invention can often be described as a slot antenna which in optional embodiments may comprise a multi-patch slot antenna which can include a microstrip feed line oriented specific to the patch design. Yet in further embodiments the antenna can also be constructed as a single patch slot design and can include more patches depending upon the requirements of the usage scenario. In optional embodiments, the lower laminate 102 can be described as a double slotted patch which is connected to the microstrip feed line 106 and thus has connection to the connector cable 302.

Optional embodiments of the antenna can also include two substrate layers where a feed line is imprinted in silver on silicone of appropriate dielectromagnetics. A second layer of silicone may then be imprinted with the patch lens antenna. When such embodiments are placed together the effect is very similar to an antenna with multiple layers. In yet further optional embodiments, additional layers of patch slot combinations can be added to modify band width and to also alter the resonance frequency so that the energy field is changed. Furthermore, the applicator of the present invention can be optimized based in part upon tissue permittivity by adjusting the size of the patches, the slot as well, as the thickness of the used substrate.

Optional aspects of the present invention include the method of using the applicator for a variety of different ailments or reasons for the patient. One such optional use may be in the primary treatment of localized solid tumors. A similar but additional optional treatment may be in the adjuvant treatment of localized solid tumors in conjunction with either radiation or chemotherapy. Additionally this treatment may also include for lymphoid tumors which can optionally include locoregional disease.

In additional optional aspects of the invention, the applicator may be used as an aid for in vivo electroporation with various pulse parameters. The applicator may be used to create a localized electromagnetic field as well as a localized thermal field.

Optional aspects of the invention may also include the capacity to include localized drug uptake within the region treated by the applicator. Additionally such treated region may optionally also experience tissue oxygenation as a result of the electromagnetic fields.

In yet further optional aspects of the present invention, applications may include for the improvement of wound healing by stimulating new collagen deposits as a result of the electromagnetic field created by the applicator.

Figure 14:
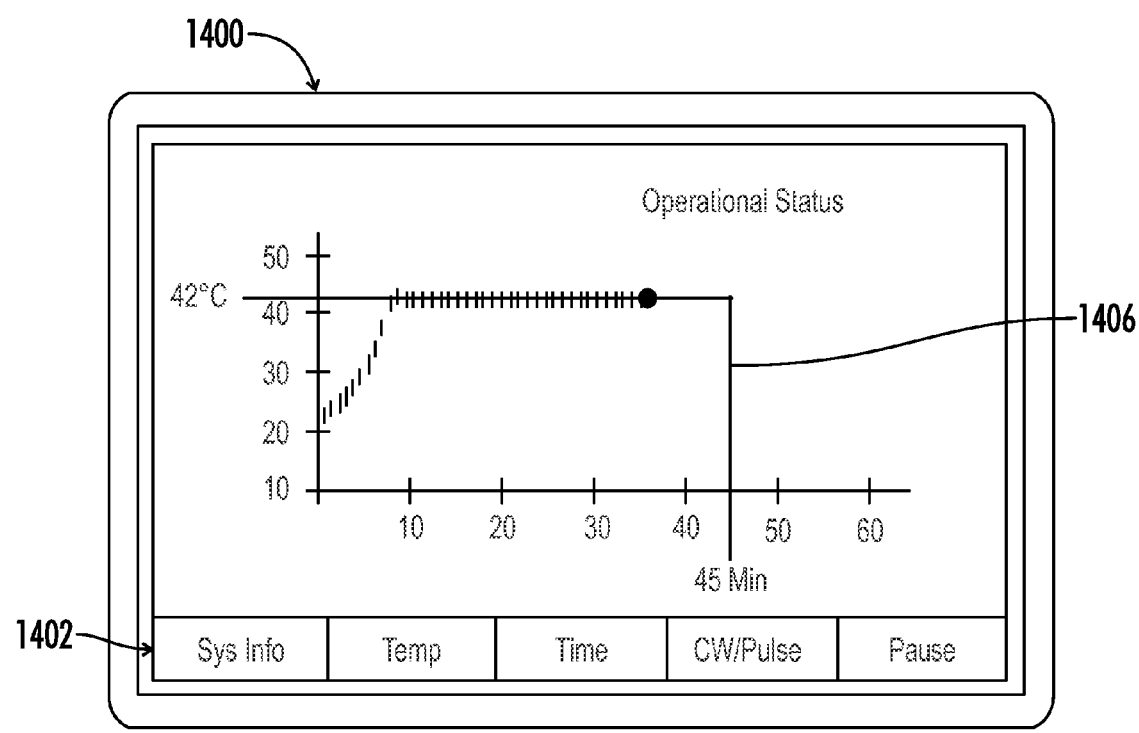
FIG. 14 is a perspective view of a display of a medical apparatus.

FIG. 14 provides a general example of a display 1400 of the medical apparatus. The display 1400 is shown including its functional visual elements for the medical apparatus. In optional embodiments, the display 1400 may be 420×270 pixels with 10×14 pixels for large characters and 8×10 pixels for small characters with 5 pixels being a minimum horizontal and 3 pixels per degree Celsius vertical. Other sizes and applications may be utilized.

In optional embodiments, a rotary encoder with a push to select switch may be located to the right of the display or alternatively at different locations though in the proximity of the display which may allow a user a selection of various treatment control functions within the display 1400. In optional embodiments, there may be five different panels 1402 across the bottom of the display 1400 which can be selected and highlighted by the user.

In more optional embodiments, by rotating an rotary encoder, a user may move the selection of different panels 1402 and thus can provide both tactile feedback as well as visual feedback for each selection. Various options may be utilized to select different choices from a push to select activation to other embodiments known in the art.

In optional embodiments, the display may also provide a temperature time graph 1406 that presents temperature over a range that may be from about 10° to about 50° C. contrasted with a temperature at treatment time over a specific interval. Such interval may be from about 0 minutes to about 60 minutes though it can be shorter or longer depending on the specific application for the patient. The user may input a desired temperature limit into the system prior to treatment by accessing the temperature panel and thus for example in the provided figure the limit of 42° C. is indicated by a straight horizontal line. The interval treatment time as displayed in the example is set at 45 minutes as indicated by the horizontal line at 45. A history of the temperature measured at the applicator pad is superimposed on the temperature time graph 1406, and thus this embodiment shows that the target temperature of about 42° C. was reached at approximately about 8 minutes after treatment began. The target temperature appears to have been maintained by controlling the radiofrequency signal driving the applicator over approximately 36 minutes of treatment.

Delivery efficiency is indicative of the power transfer (see i.e., absorbed power) into the subcutaneous area of the patient adjacent the antenna (i.e., applicator) connected to the output of the medical apparatus. Thus, by maximizing subcutaneous heating, skin surface heating is minimized. This allows increased subcutaneous temperatures over prior art systems, providing a more effective therapy. Determining the delivery efficiency of the medical apparatus is made possible by use of the bidirectional coupler in a control unit of the medical apparatus to distinguish an output signal (i.e., the radiofrequency signal driving the applicator and antenna) from a reflected signal.

Figure 15:
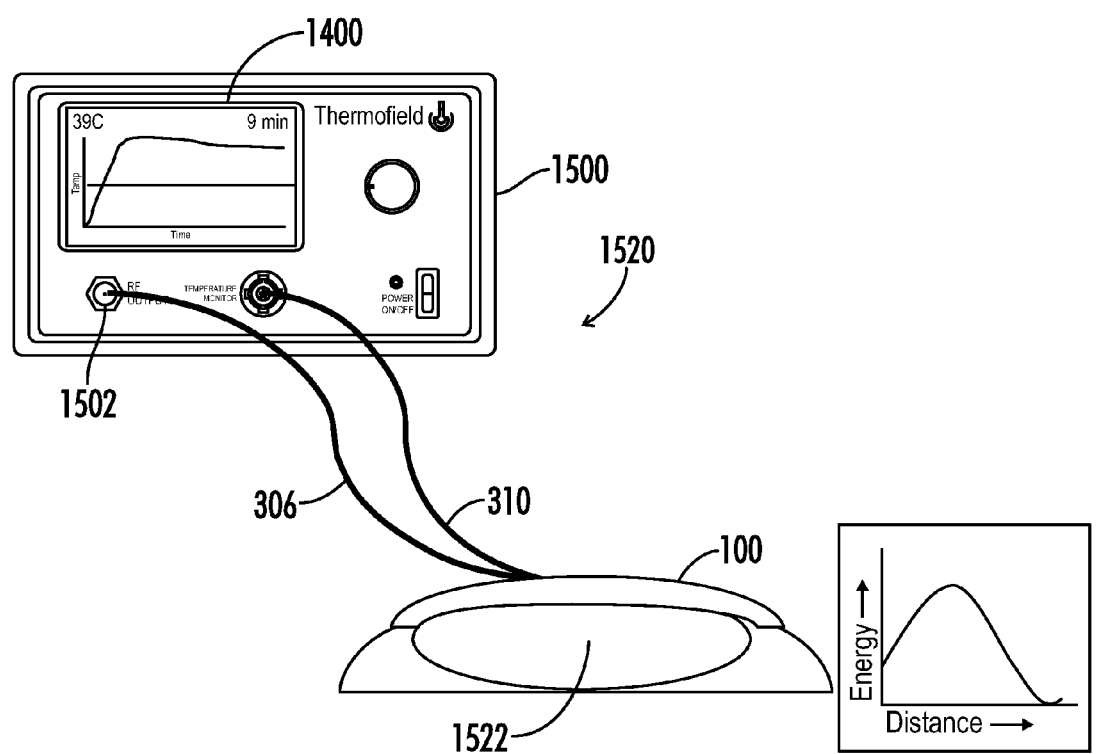
FIG. 15 is a perspective view of a medical apparatus.

Referring to FIG. 15, a medical apparatus 1520 operable to induce localized hyperthermia 1522 in a patient via an electromagnetic field emitted by an antenna connected to an output 1502 of the medical apparatus 1520 includes a control unit 1500, the connector cable 306, and the applicator 100 including the antenna. Optionally, the applicator 100 includes the temperature sensor 302, and the medical apparatus 1520 further includes the temperature sensor cable 310 connecting the temperature sensor 302 to the control unit 1500.

Figure 16:
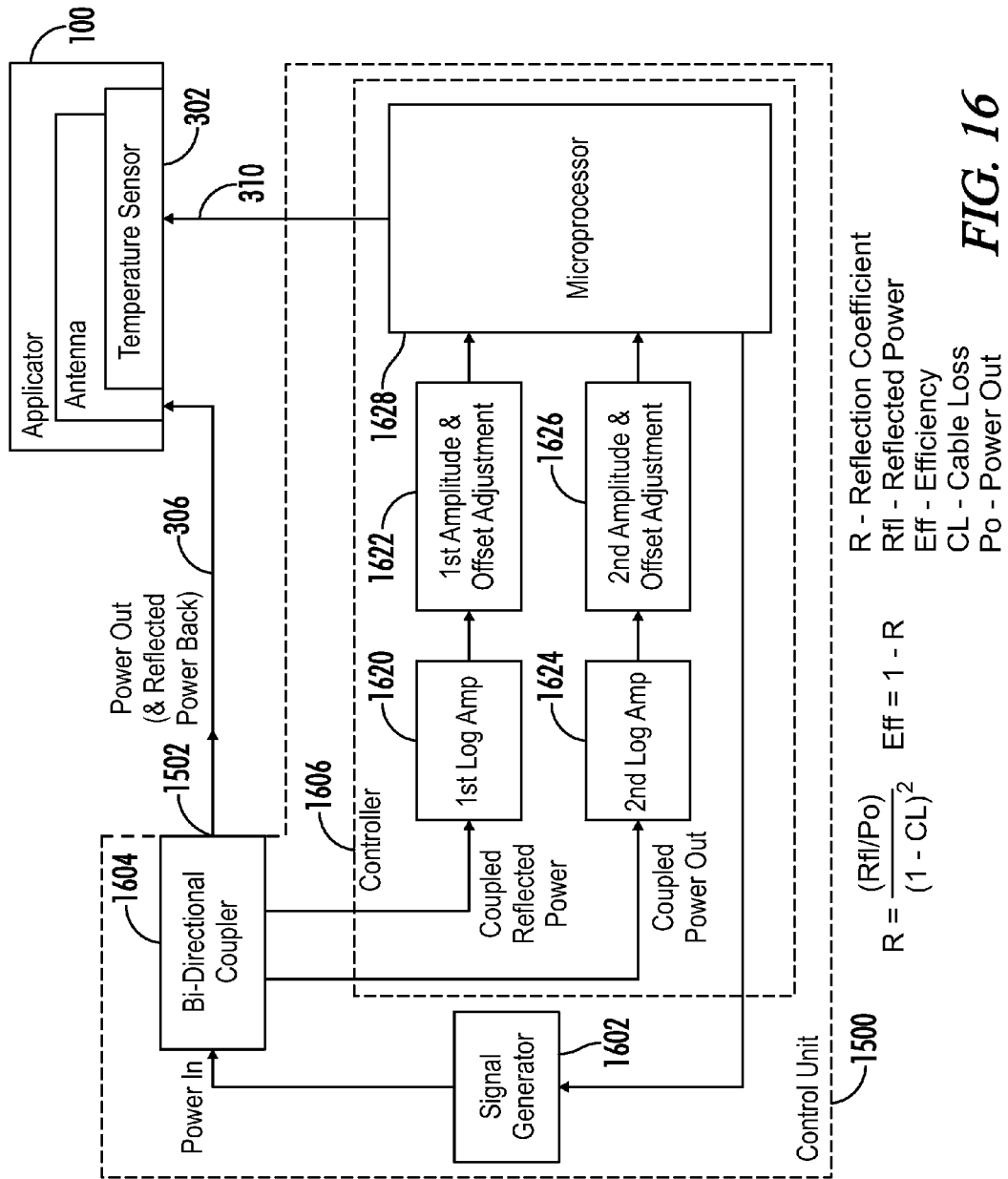
FIG. 16 is a partial block diagram of a medical apparatus operable to induce localized hyperthermia in a patient.

Referring to FIG. 16, the control unit 1500 of the medical apparatus 1520 of FIG. 15 includes a signal generator 1602, a bidirectional coupler 1604, and a controller 1606. The control unit 1500 also includes a power source (not shown) operable to provide power to components of the control unit 1500. One skilled in the art will understand that various power sources such as batteries and/or powerline power may be used to provide power to the components of the control unit 1500 during operation.

The signal generator 1602 is operable to generate radio frequency signal and provide the generated radiofrequency signal to the bidirectional coupler 1604. The bidirectional coupler 1604 is connected to the signal generator 1602 and to the output 1502 of the medical apparatus 1520. In one embodiment, the output 1502 of the medical apparatus 1520 is synonymous with the output of the bidirectional coupler 1502 and with the output of the control unit 1500. The bidirectional coupler 1604 provides the radiofrequency signal generated by the signal generator 1602 to the output 1502 and receives a reflected signal from the output 1502. Generally, the reflected signal is the signal reflected by the antenna of the applicator 100 via the connector cable 306.

The controller 1606 is connected to the bidirectional coupler 1604 and the signal generator 1602. In one embodiment, the controller 1606 is connected to the signal generator 1602 via an input section of the bidirectional coupler 1604 to receive the radio frequency signal. In another embodiment, the controller 1606 is directly connected to the signal generator 1602 to receive the radiofrequency signal directly from the signal generator 1602. The controller 1606 is operable to determine a power of the radiofrequency signal generated by the signal generator 1602. The controller 1606 also receives the reflected signal from the bidirectional coupler 1604, and determines a power of the reflected signal. The controller 1606 then determines a delivery efficiency of the medical apparatus 1520 as a function of the determined power of the radiofrequency signal generated by the signal generator 1602 and the determined power of the reflected signal. In one embodiment, the delivery efficiency is determined by EQUATION 1.

$$DeliveryEfficiency = 1 - \frac{(Rfl/Po)}{(1-CL)^2} \quad \text{EQUATION 1}$$

Similarly, the controller 1606 may determine the power absorbed by the localized area of the patient adjacent the applicator 100 via EQUATION 2.

$$AbsorbedPower = Po \times (1-CL) \times DeliveryEfficiency \quad \text{EQUATION 2}$$

In EQUATIONS 1 and 2, Rfl is the determined power of the reflected signal, Po is the determined power of the radiofrequency signal generated by the signal generator 1602, and CL is a cable loss coefficient dependent on the connector cable 306. In one embodiment, the connector cable 306 is a 4 foot long coaxial 50 ohm transmission cable having a cable loss coefficient of 0.129.

In one embodiment, the display 1400 is also connected to the controller 1606. The controller 1606 provides the determined delivery efficiency to the display 1400, and the display 1400 displays the delivery efficiency to a user (i.e., a caregiver or healthcare provider). It is contemplated that the user and patient may be one in the same under certain circumstances.

In one embodiment, the medical apparatus 1520 also includes the temperature sensor 302 of the applicator 100. The temperature sensor 302 measures a skin temperature of the patient adjacent the antenna of the applicator. That is, the temperature sensor 302 may be directly against the skin of the patient, or the temperature at the skin of the patient (i.e., the skin temperature of the patient) may be approximated as the temperature in the applicator 100 near the skin of the patient. The controller 1606 may adjust an operating parameter of the signal generator 1602 to reduce power delivered to the patient by the medical apparatus 1520 in response to determining that the skin temperature exceeds a predetermined threshold (e.g., 42° C.).

One embodiment, the signal generator 1602 generates the radio frequency signal as a function of operating parameters received from the controller 1606. In this way, the controller 1606 controls the signal generator 1602 and the radiofrequency signal generated by the signal generator 1606. The radiofrequency signal generated by the signal generator 1602 may be a pulse width modulated signal having a base frequency between 400 and 460 MHz or between 890 and 950 MHz. The pulse width modulation may be between 1 and 10 Hz. That is, the pulse width modulation may be between one and 10 pulses per second (pps) or have a period of 0.1 seconds to 1 second. A duty cycle of the radiofrequency signal may vary between 0 and 100%. Thus, in one embodiment, the operating parameters provided to the signal generator 1602 by the controller 1606 are a frequency, a power level, a duty cycle, and a pulses per second (i.e., period or pulse width modulation frequency). In one embodiment, the power level is variable from 2 to 40 Watts with therapy provided between 10 and 40 Watts (e.g., 10 Watts, 20 Watts, 30 Watts, or 40 Watts), and a 2 W mode of operation for adjusting the applicator 100 on the patient to maximize delivery efficiency. In one embodiment, the power level is adjusted by the controller 1606 to maintain the skin temperature of the patient as determined via the temperature sensor 302 at a predetermined temperature (e.g., 42° C.).

In one embodiment, the controller 1606 is operable to automatically optimize the operating parameters provided to the signal generator 1602 in order to maximize delivery efficiency. The controller steps the radiofrequency signal through a plurality of operating parameters (e.g., sweeps the base frequency from 400 to 460 MHz in 10 MHz increment steps or sweeps the pulses per second from one pulse per second to 10 pulses per second in one pulse per second increment steps). The controller 1606 determines the delivery efficiency at each of the plurality of operating parameters (e.g. at each base frequency step or pulses per second step). The controller 1606 then determines the operating parameter of the plurality of operating parameters having the highest determined delivery efficiency. The controller 1606 then controls the signal generator 1602 to continue operation of the signal generator 1602 at the operating parameter of the plurality of operating parameters determined to have the highest delivery efficiency. That is, the controller 1606 selects the operating parameter resulting in the highest delivery efficiency and continues providing that operating parameter for the remainder of the therapy session. The operating parameter may be the duty cycle, the power level, the frequency, or the pulses per second of the radiofrequency signal.

The controller 1606 includes a first logarithmic amplifier 1620, a first amplitude and offset compensation circuit 1622, a second logarithmic amplifier 1624, a second amplitude and offset compensation circuit 1626, and a microprocessor 1628. The first logarithmic amplifier 1620 is connected to the bidirectional coupler 1604 to receive the reflected signal from the bidirectional coupler 1604 and provide an amplified reflected signal. The first amplitude and offset compensation circuit 1622 is connected to the first logarithmic amplifier 1620. The first amplitude and offset compensation circuit 1622 receives the amplified reflected signal from the first logarithmic amplifier 1620 and provides a digital representation of the reflected signal to the microprocessor 1628. The second logarithmic amplifier 1624 is connected to the signal generator 1602 (either directly or via an input section of the bidirectional coupler 1604). The second logarithmic amplifier 1624 receives the radiofrequency signal from the signal generator 1602 and provides an amplified radio frequency signal. The second amplitude and offset compensation circuit 1626 is connected to the second logarithmic amplifier 1624. The second amplitude and offset compensation circuit 1626 receives the amplified radio frequency signal from the second logarithmic amplifier 1624 and provides a digital representation of the radiofrequency signal to the microprocessor 1628. The processor 1628 is connected to the first amplitude and offset compensation circuit 1622, to the second amplitude and offset compensation circuit 1626, and optionally to the temperature sensor 302. The processor 1628 may include input buffer circuitry to modify and digitize a signal received from the temperature sensor 302. The processor 1628 receives the digital representation of the reflected signal from the first amplitude and offset compensation circuit 1622 and the digital representation of the radiofrequency signal from the second amplitude and offset compensation circuit 1626. The processor 1628 determines the delivery efficiency of the medical apparatus 1520 based on the received digital representation of the reflected signal and the received digital representation of the radiofrequency signal.

Figure 17:
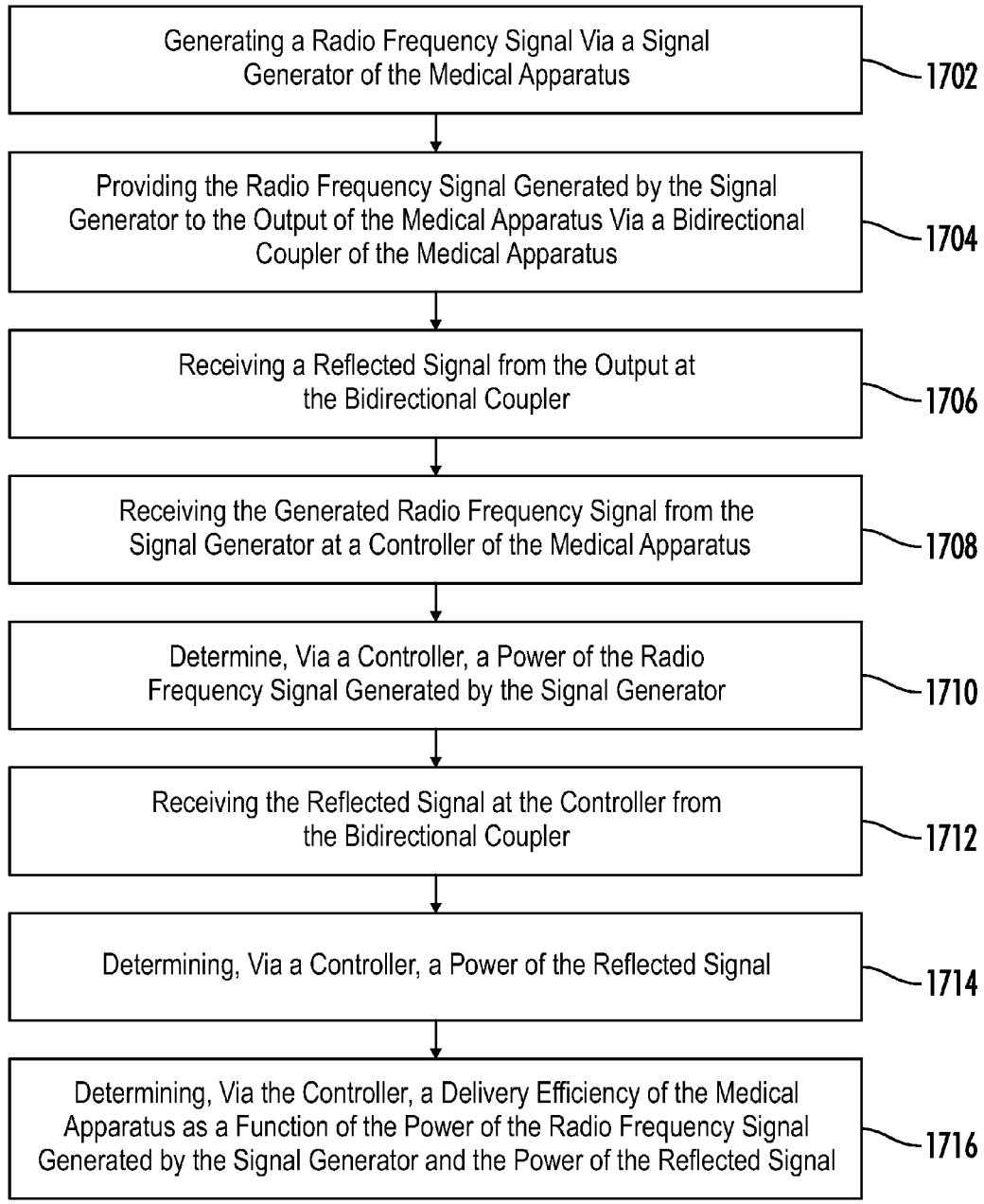
FIG. 17 is a flowchart of a method of inducing localized hyperthermia in a patient via an electromagnetic field.

Referring to FIG. 17, a method of inducing localized hyperthermia in a patient via an electromagnetic field emitted by an antenna connected to an output (e.g., the output 1502) of a medical apparatus (e.g., the medical apparatus 1520) is disclosed with respect to the medical apparatus 1520. The method begins at 1702 with generating a radiofrequency signal via the signal generator 1602 of the medical apparatus 1520. The radiofrequency signal generated by the signal generator 1602 is provided to the output 1502 of the medical apparatus 1520 via a bidirectional coupler 1604 of the medical apparatus 1520 at 1704. At 1706, a reflected signal is received from the output 1502 at the bidirectional coupler 1604. At 1708, the generated radiofrequency signal from the signal generator 1602 is received at the controller 1606 of the medical apparatus 1520. The controller 1606 determines a power of the radiofrequency signal generated by the signal generator 1602 at 1710. At 1712, the reflected signal received at the controller 1606 from the bidirectional coupler 1604, and that 1714 the controller 1606 determines a power of the reflected signal. It 1716, the controller 1606 determines a delivery efficiency of the medical apparatus 1520 as a function of the determined power of the radiofrequency signal generated by the signal generator 1602 and determined power of the reflected signal from the bidirectional coupler 1604. As described above with respect to the medical apparatus 1520, the method may optionally include automatically stepping through operating parameters of the signal generator in order to optimize the delivery efficiency of the method.

As described above with respect to the medical apparatus 1520, the controller 1606 (especially processor 1628) may determine the delivery efficiency of the medical apparatus 1520 as a function of the determined power of the radiofrequency signal and the determined power of the reflected signal. To determine the delivery efficiency, the processor 1628 determines a quotient of the reflected power divided by the power of the radiofrequency signal. The processor 1628 also determines a difference of 1 minus a cable loss of the connector cable 306. The processor 1628 then determines a square of the difference. The processor 1628 determines a reflection coefficient by dividing the quotient by the square. Subtracting the reflection coefficient from 1 yields the delivery efficiency.

It is contemplated that the signal generator 1602 and/or the bidirectional coupler 1604 may be integral with the controller 1606 within the scope of the claims. It is also contemplated that components of the controller 1606 (e.g., the 1st logarithmic amplifier 1620, the 1st amplitude and offset compensation circuit 1622, the 2nd logarithmic amplifier 1624, and/or the 2nd amplitude and offset compensation circuit 1626) may be constructed integrally with the microprocessor 1628 or in separate components within the scope of the claims.

In yet further optional embodiments, various other settings may be utilized including wider or smaller temperature ranges as well as shorter or longer durations of time. By using these specific values for the sake of explaining the invention, applicant by no means intends to limit the applicant to the specific values previously described.

In even further optional embodiments of the control system for the applicator, faults may be reported through the system and handled by the medical apparatus. Generally the faults may include both hard and soft faults where hard faults are considered potentially harmful to the equipment which may in turn pose a threat to treatment whereas soft faults are expected occasionally and are generally not expected to be damaging or harmful to the equipment. As faults are expected to happen on occasion the system may optionally be configured so as to report and provide information about the fault that may have occurred.

In yet further optional embodiments the radio frequency parameters may be adjustable for a specific system. This may be controlled through the medical apparatus treatment settings and for example in some instances the frequency of the radiofrequency signal driving the applicator may be adjusted from 400 MHz to 460 MHz in 10 MHz steps. Similarly, power parameters may also be adjusted for the system and can include adjustments from about 2 watts to up to 40 watts. Various wattages may be utilized and the user can select specific wattages between the maximum and minimum wattage and in some instances increments in 10 watt steps may be utilized.

Furthermore, during treatment, various options may be adjustable including specific temperature (i.e., target temperature or maximum temperature) as well as the treatment time and other variables in between. Other options that may be adjusted in optional embodiments of the control system for the applicator can include a change to the administration of the electromagnetic field from a constant output to a pulse width modulated arrangement and back and forth. In optional arrangements, pulse therapy (i.e., pulse width modulation) may be more beneficial to a user than a constant input from an electromagnetic field. As such, a user may change such feature throughout the treatment or prior to treatment and can adjust the length of pulse or the intensity. Alternatively, the medical apparatus may determine the mode of operation providing the highest delivery efficiency and automatically select that mode of operation.

In various embodiments of the present invention, the medical apparatus may include or be linked to a database which may be effective to store various parameters associated with a plurality of conditions, diseases, ailments or the like for which a user may want to provide treatment therefor. As such, the database may also store default settings for treatment associated with various patient species as well as conditions and may include specific regimens stored by the health care provider. Further optional embodiments may include a database that may be sorted to the specific patient so that the health care provider can create a template and/or specific program for a patient for an extended duration and maintain that template.

In various optional embodiments, the applicator may be used for a variety of different applications. These may include nosocomial infections also known as hospital acquired infections which can be associated with various microorganisms as well as bacteria. Other applications may include the treatment of diabetic foot ulcers. Other applications may include use for wound management and/or bed sores so as to alleviate pain experienced by a patient.

Further applications may include the system being used as an electronic contrast agent which can include uses for image technologies as previously mentioned.

Other ailments may also be affected through the use of the applicator of the present invention which can include skin conditions such as psoriasis, acne and cellulite.

Additional ailments which may be treated can include symptoms of Parkinson's disease where users may experience lessened effects of the neurological problems associated with Parkinson's through treatment.

Other applications may include the use of the system for sterilizing purposes for a dialysis machine.

Other muscle and joint disorders can be treated through the use of the medical apparatus of the present invention which include temporomandibular muscle and joint disorders as well as non-invasive forms of dialysis pain management for sports medicines. In other optional embodiments, including carpal tunnel syndrome and other painful musculoskeletal issues including lateral epicondylitis (tennis elbow), rotor cuff tears, meniscus tears, and trochanteric bursitis can be treated. Other applications can include the treatment of plantar fasciitis, chronic back pain, osteoarthritis, rheumatoid arthritis, gouty arthritis and even dysmenorrhea.

In yet further optional embodiments of the invention, while the applicator has been described as being flexible, other forms of the applicator may include a cylindrical shape. Such cylindrical shape may be used in instances where anatomical features cannot be properly treated with just a flat style applicator. Such optional embodiments with a cylindrical or elongated design may be used as a type of applicator for providing internal treatment which can include the insertion into various orifices on a patient. This can include and range from treatment options from cancer of the prostate to vaginal or cervical cancer as well as a potential treatment for various forms of colon cancer. Furthermore, the cylindrical shape can be designed so that the field permeates from one specific location upon the cylinder so that the electromagnetic field may be focused. However in optional embodiments, a variety of different antenna can be utilized with the cylindrical applicator and thus a user may chose the specific applicator that best suits the usage scenario.

As previously mentioned, aspects of optional embodiments of the present invention may include a temperature sensor and controller that may maintain the substrate (and thus the patient's skin adjacent the applicator) at a predetermined temperature. In these optional embodiments, the temperature control and sensor may be placed centrally in the antenna although in other optional embodiments may be located at various locations upon the antenna which may in part be based upon the size of the applicator as well as the specific anatomical location for which the applicator will be used.

As also discussed, the antenna as used in the various optional embodiments of the present invention can often be described as a slot antenna which in optional embodiments may comprise a multi-patch slot antenna which can include a microstrip feed line oriented specific to the patch design. Yet in further embodiments, the antenna can also be constructed as a single patch slot design and yet further can include even more patches just depending upon the desires of the user. Furthermore, in optional embodiments the upper laminate can be described as a double slotted patch which is connected to the microstrip feed line and thus has connection to the coaxial cable.

Optional embodiments of the antenna can also include two substrate layers where a feed line is imprinted in silver on silicone of appropriate dielectromagnetics. A second layer of silicone may then be imprinted with the antenna. When such embodiments are placed together the effect is very similar to an antenna with multiple layers. In yet further optional embodiments, additional layers of patch slot combinations can be added to modify band width and to also alter the resonance frequency so that the electromagnetic field is changed for the specific application for the patient. Furthermore, the applicator of the present invention can be optimized based in part upon tissue permittivity by adjusting the size of the patches the slot as well as the thickness of the used substrate.

As also has been discussed, optional aspects of the present invention include the method of using the applicator for a variety of different ailments or reasons for the patient. One such optional use may be in the primary treatment of localized solid tumors. A similar but additional optional treatment may be in the adjuvant treatment of localized solid tumors in conjunction with either radiation or chemotherapy. Additionally this treatment may also include for lymphoid tumors which can optionally include locoregional disease.

Further optional uses of the invention of the above-captioned application may be to improve local blood profusion including cutaneous and visceral perfusion.

In yet further optional aspects of the present invention applications may include for the improvement of wound healing by stimulating new collagen deposits as a result of the electromagnetic field created by the applicator.

Yet further optional aspects of the present invention may lead to increased local concentration of administered macromolecules. Otherwise stated this may include interaction with heavy metal compounds such as platinum chemotherapeutics which can lead to local drug concentrations. Increased concentration may be achieved in part through the accumulation of nanoparticles and drugs trapped based upon the physiologic charge of the moieties. Yet further such application may be used to increase the local tissue concentration of other charged moieties which may include antibiotics or DNA/RNA nucleotides which may be used in gene therapeutics.

Yet even further optional aspects of the present invention may be used for the purpose of the adjuvant treatment of osteoarthritis as well as the adjuvant treatment of neurogenetic pain, adjuvant treatment of musculoskeletal pain and additionally may be used to improve tendon healing or tissue perfusion prior to exercise.

In yet additional optional aspects of the present invention, the medical apparatus may be used to provide an electromagnetic field that can be used as a non-invasive contrast agent to assist in ultrasound and MRI imaging. Similarly, the electromagnetic field generated by the antenna can be used as a contrast agent to assist in detection of inflammatory neoplastic or degenerative lesions.

In further optional embodiments of the present invention the medical apparatus may be associated with software residing on either a computer or network. Generally a host system may be utilized with the present invention and may include one or more data processors as well as a graphic user interface computer readable memory containing a computer program executable by one or more data processors using techniques as are well known in the art. In some embodiments a single membrane medium may be provided which is effective to store software useful for the applicator and any data which is received in relation to the program. In other embodiments a plurality of memory media including that containing the computer program as well as one or more databases or equivalent storage entities may be provided and functionally linked to collectively perform the functions of the system as described herein.

As described briefly with regard to the optional software aspects of the invention, various controls and operating parameters can be used for treating a patient. In many optional embodiments, power output may be controlled automatically through feedback from the antenna temperature sensor and feedback from the applicator. Such design can allow for maximal power during the initial heating and a reduction to near zero at or above the desired target temperature.

Yet furthermore, optional aspects may further include a pulse feature where one could tailor pulse repetitions or pulse width in duty cycle which can in part be based upon feedback from the temperature sensor to the control unit. For example, during the initial heating of the patient, the intervals can be shortened so as to speed up acquisition of a preset target temperature. Subsequently, at the desired temperature the values can be adjusted to maintain a constant surface temperature.

For various applications for species of animals with tumors that may be considered stage 3 or higher, often eight to twelve treatments using the medical apparatus of the present invention may be necessary to provide treatment. General treatment times for a localized region range from about 20 minutes to about 40 minutes though can be shorter or longer. Often the time to reach a surface temperature of greater than or equal to 39 degrees Celsius range from about six minutes to about 15 minutes though could be longer or shorter. Time to reach a optionally considered maximum temperature can range from about eight minutes to about twenty-three minutes. Obviously these times can be longer or shorter and not meant to be limiting upon the invention. Rather, they are provided as possible ranges and variants for treatment.

In administering hyperthermic treatment by way of the inventive applicator, response times range from about one week to eight weeks, with averages possibly being around four and one half week or so for some animals. In some patients, a complete response may be seen whereas in other patients there may be a temporary delay or slowing of the tumor growth.

Advantageously the medical apparatus of the present invention may preclude the use of a water bolus as the skin of a patient remains cooler than prior art designs. Otherwise stated, the applicators as disclosed herein may focus the energy transmission and thus not require the increased voltage as does prior art devices and therefore is less likely to burn a patient's skin. Thus, an optional aspect of the invention is a use of an applicator without a water bolus for treatment of a patient.

Furthermore, sizes of various structural parts and materials used to make the above mentioned components are illustrative and exemplary only, and persons of ordinary skill in the art would recognize that these sizes and materials can be changed as necessary to produce different results or different desired characteristics.

It will be understood by those of skill in the art that information and signals may be represented using any of a variety of different technologies and techniques (e.g., data, instructions, commands, information, signals, bits, symbols, and chips may be represented by voltages, currents, electromagnetic waves, magnetic fields or particles, optical fields or particles, or any combination thereof). Likewise, the various illustrative logical blocks, modules, circuits, and algorithm steps described herein may be implemented as electronic hardware, computer software, or combinations of both, depending on the application and functionality. Moreover, the various logical blocks, modules, and circuits described herein may be implemented or performed with a general purpose processor (e.g., microprocessor, conventional processor, controller, microcontroller, state machine or combination of computing devices), a digital signal processor ("DSP"), an application specific integrated circuit ("ASIC"), a field programmable gate array ("FPGA") or other programmable logic device, discrete gate or transistor logic, discrete hardware components, or any combination thereof designed to perform the functions described herein. Similarly, steps of a method or process described herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. Although embodiments of the present invention have been described in detail, it will be understood by those skilled in the art that various modifications can be made therein without departing from the spirit and scope of the invention as set forth in the appended claims.

A controller, processor, computing device, client computing device or computer, such as described herein, includes at least one or more processors or processing units and a system memory. The controller may also include at least some form of computer readable media. By way of example and not limitation, computer readable media may include computer storage media and communication media. Computer readable storage media may include volatile and nonvolatile, removable and non-removable media implemented in any method or technology that enables storage of information, such as computer readable instructions, data structures, program modules, or other data. Communication media may embody computer readable instructions, data structures, program modules, or other data in a modulated data signal such as a carrier wave or other transport mechanism and include any information delivery media. Those skilled in the art should be familiar with the modulated data signal, which has one or more of its characteristics set or changed in such a manner as to encode information in the signal. Combinations of any of the above are also included within the scope of computer readable media.

This written description uses examples to disclose the invention and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

It will be understood that the particular embodiments described herein are shown by way of illustration and not as limitations of the invention. The principal features of this invention may be employed in various embodiments without departing from the scope of the invention. Those of ordinary skill in the art will recognize numerous equivalents to the specific procedures described herein. Such equivalents are considered to be within the scope of this invention and are covered by the claims.

All of the compositions and/or methods disclosed and claimed herein may be made and/or executed without undue experimentation in light of the present disclosure. While the compositions and methods of this invention have been described in terms of the embodiments included herein, it will be apparent to those of ordinary skill in the art that variations may be applied to the compositions and/or methods and in the steps or in the sequence of steps of the method described herein without departing from the concept, spirit, and scope of the invention. All such similar substitutes and modifications apparent to those skilled in the art are deemed to be within the spirit, scope, and concept of the invention as defined by the appended claims.

Thus, although there have been described particular embodiments of the present invention of a new and useful APPARATUS AND METHOD FOR HYPERTHERMIC

TREATMENTS it is not intended that such references be construed as limitations upon the scope of this invention except as set forth in the following claims.

What is claimed is:

1. A method of inducing localized hyperthermia in a patient via an electromagnetic field emitted by an antenna connected to an output of a medical apparatus, said method comprising:
   generating a radio frequency signal via a signal generator of the medical apparatus;
   providing the radio frequency signal generated by the signal generator to the output of the medical apparatus via a bidirectional coupler of the medical apparatus;
   receiving a reflected signal from the output at the bidirectional coupler;
   receiving the generated radio frequency signal from the signal generator at a controller of the medical apparatus;
   determining, via the controller, a power of the radio frequency signal generated by the signal generator;
   receiving the reflected signal at the controller from the bidirectional coupler;
   determining, via the controller, a power of the reflected signal; and
   determining, via the controller, a delivery efficiency of the medical apparatus as a function of the power of the radio frequency signal generated by the signal generator and the power of the reflected signal;
   wherein determining, via the controller, the delivery efficiency of the medical apparatus as a function of the power of the radio frequency signal generated by the signal generator and the power of the reflected signal comprises:
      determining a quotient of the reflected power divided by the power of the radio frequency signal;
      determining a difference of 1 minus a cable loss of a connector cable of the medical apparatus;
      determining a square of the difference; and
      determining a reflection coefficient by dividing the quotient by the square; and
      subtracting the reflection coefficient from one to yield the delivery efficiency.

2. The method of claim 1, further comprising:
   providing the determined delivery efficiency to a display of the medical apparatus; and
   displaying the delivery efficiency to a user via the display of the medical apparatus.

3. The method of claim 1, further comprising:
   measuring a skin temperature of the patient adjacent the antenna via a temperature sensor connected to the controller of the medical apparatus;
   determining whether the skin temperature exceeds a predetermined threshold; and
   adjusting an operating parameter of the signal generator in response to determining that the skin temperature exceeds the predetermined threshold, wherein adjusting the operating parameter reduces power delivered to the patient by the medical apparatus.

4. The method of claim 1, wherein the signal generator generates the radio frequency signal as a function of an operating parameter provided by the controller, and wherein said method further comprises:
   providing a frequency for the radio frequency signal to the signal generator from the controller;
   providing a power level for the radio frequency signal to the signal generator from the controller;
   providing a duty cycle for the radio frequency signal to the signal generator from the controller; and
   providing a pulses per second of the radio frequency signal to the signal generator from the controller.

5. The method of claim 1, wherein the signal generator generates the radio frequency signal as a function of an operating parameter provided by the controller, said method further comprising:
   controlling, via the controller, the signal generator to step the radio frequency signal through a plurality of operating parameters;
   determining, via the controller, the delivery efficiency while the radio frequency signal is generated based on each of the plurality of operating parameters;
   determining the operating parameter of the plurality of operating parameters resulting in the highest delivery efficiency; and
   continuing operation of the signal generator at the operating parameter of the plurality of operating parameters determined to have the highest delivery efficiency by continuing to provide the operating parameter of the plurality of operating parameters determined to have the highest delivery efficiency from the controller to the signal generator.

6. The method of claim 5, wherein the operating parameter is a duty cycle, a power level, a frequency, or a pulses per second of the radio frequency signal.

7. The method of claim 1, wherein the signal generator generates the radio frequency signal as a function of a frequency provided by the controller, said method further comprising:
   controlling, via the controller the signal generator to step the radio frequency signal through a plurality of frequencies;
   determining, via the controller, the delivery efficiency while the radio frequency signal is generated based on each of the plurality of frequencies;
   determining the frequency of the plurality of frequencies resulting in the highest delivery efficiency; and
   continuing operation of the signal generator at the frequency of the plurality of frequencies determined to have the highest delivery efficiency by continuing to provide the frequency of the plurality of frequencies determined to have the highest delivery efficiency from the controller to the signal generator.

8. The method of claim 1, wherein the signal generator generates the radio frequency signal as a function of a duty cycle provided by the controller, said method further comprising:
   controlling, via the controller the signal generator to step the radio frequency signal through a plurality of duty cycles;
   determining, via the controller, the delivery efficiency while the radio frequency signal is generated based on each of the plurality of duty cycles;
   determining the duty cycle of the plurality of duty cycles resulting in the highest delivery efficiency; and
   continuing operation of the signal generator at the duty cycle of the plurality of duty cycles determined to have the highest delivery efficiency by continuing to provide the duty cycle of the plurality of duty cycles determined to have the highest delivery efficiency from the controller to the signal generator.

9. The method of claim 1, wherein the signal generator generates the radio frequency signal as a function of a pulses per second provided by the controller, said method further comprising:

controlling, via the controller the signal generator to step the radio frequency signal through a plurality of pulses per second;

determining, via the controller, the delivery efficiency while the radio frequency signal is generated based on each of the plurality of pulses per second;

determining the pulses per second of the plurality of pulses per second resulting in the highest delivery efficiency; and continuing operation of the signal generator at the pulses per second of the plurality of pulses per second determined to have the highest delivery efficiency by continuing to provide the pulses per second of the plurality of pulses per second determined to have the highest delivery efficiency from the controller to the signal generator.

* * * * *